US007625731B2

United States Patent
Mosyak et al.

(10) Patent No.: US 7,625,731 B2
(45) Date of Patent: Dec. 1, 2009

(54) AGGRECANASE STRUCTURE

(75) Inventors: Lydia Mosyak, Newton, MA (US); Thomas Saltmarsh Rush, III, Lexington, MA (US); Stephane Hubert Olland, Arlington, MA (US); Edward R. LaVallie, Harvard, MA (US); Lisa A. Collins-Racie, Acton, MA (US); Christopher John Corcoran, Arlington, MA (US); Stewart Andrews Mackie, Rye Beach, NH (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 11/467,138

(22) Filed: Aug. 24, 2006

(65) Prior Publication Data

US 2007/0105207 A1    May 10, 2007

Related U.S. Application Data

(60) Provisional application No. 60/711,457, filed on Aug. 25, 2005.

(51) Int. Cl.
| | |
|---|---|
| *C12N 9/00* | (2006.01) |
| *C12N 11/16* | (2006.01) |
| *C12N 9/14* | (2006.01) |
| *C12N 9/48* | (2006.01) |
| *C12N 9/50* | (2006.01) |
| *C12N 9/64* | (2006.01) |

(52) U.S. Cl. ................ 435/183; 435/174; 435/195; 435/212; 435/219; 435/226

(58) Field of Classification Search ............ None
See application file for complete search history.

(56) References Cited

U.S. PATENT DOCUMENTS

| | | |
|---|---|---|
| 2002/0160492 A1 | 10/2002 | Cook et al. |
| 2005/0130973 A1 | 6/2005 | Xiang et al. |
| 2005/0143422 A1 | 6/2005 | Levin et al. |
| 2005/0277175 A1 | 12/2005 | LaVallie et al. |
| 2007/0178574 A1 | 8/2007 | Mosyak et al. |

FOREIGN PATENT DOCUMENTS

WO    WO 2004/011637 A2    2/2004

OTHER PUBLICATIONS

Branden et al., "Introduction to Protein Structure Second Edition", Garland Publishing Inc., New York, 1999.*
Drenth, "Principles of X-ray Crystallography," Springer, New York, 1995.*
Kierzek et al., Biophys Chem 91:1-20, 2001.*
Nagar et al., Crystal structures of the kinase domain of c-Abl in complex with the small molecule inhibitors PD173955 and Imatinib (STI-571), Cancer Research, vol. 62, p. 4236-4243, 2002.*
Medline search results for "aggrecanase-2", Retrieved from the Internet <URL: http://www.ncbi.nlm.nih.gov/sites/entrez>.*
"The CCP4 Suite: Programs for Protein Crystallography," Acta Crystallogr. Sect. D 50:760-763 (1994).
Abbaszade et al., "Cloning and Characterization of ADAMTS11, an Aggrecanase from the ADAMTS Family" J. Biol. Chem., 274(33):23443-23450 (1999).
Arner et al., "Aggrecanase. A target for the design of inhibitors of cartilage degradation" Ann N Y Acad Sci., 878:92-107 (1999).
Arner et al., "Generation and characterization of aggrecanase. A soluble, cartilage-derived aggrecan-degrading activity" J. Biol Chem., 274(10):6594-6601 (1999).
Arner, "Aggrecanase-mediated cartilage degradation" Curr. Opin Pharmacol. 2(3):322-329 (2002).
De La Fortelle et al., "Maximum-likelihood heavy-atom parameter refinement for multiple isomorphous replacement and multiwavelength anomalous diffraction methods," Methods Enzym., 276:472-494 (1997).
Hedlund et al., "Association of the aggrecan keratan sulfate-rich region with collagen in bovine articular cartilage," J Biol Chem. 274(9):5777-81 (1999).
Liu et al., "Aggrecanase: The Family and Its Inhibitors" Curr. Med. Chem.-Anti-Inflammatory & Anti-Allergy Agents 4:251-264 (2005).
Porter et al., "The ADAMTS Metalloproteinases" Biochem J. 386(1):15-27 (2005).
Rao, B.G., "Recent Developments in the Design of Specific Matrix Metalloproteinase Inhibitors Aided by Structural and Computational Studies", Current Pharm. Design, 11:295-322 (2005).
Rush et al., "The application of x-ray, NMR, and molecular modeling in the design of MMP inhibitors," Current Med. Chem. 4:1311-1327 (2004).
Seals et al., "The ADAMs family of metalloproteases: multidomain proteins with multiple functions," Genes Dev. 17(1):7-30 (2003).
Skiles et al., "The Design, Structure, and Clinical Update of Small Molecular Weight Matrix Metalloproteinase Inhibitors", Current Med. Chem., 11:2911-2977 (2004).
Skiles et al., "The Design, Structure, and Therapeutic Application of Matrix Metalloproteinase Inhibitors", Current Med. Chem., 8:425-474 (2001).
Tortorella et al., "Purification and Cloning of Aggrecanase-1: A Member of the ADAMTS Family of Proteins", Science 284:1664-1666 (1999).
Yasumoto et al., "The G1 Domain of Aggrecan Released from Porcine Articular Cartilage Forms Stable Complexes with Hyaluronan/Link Protein", Rheumatology 42(2):336-342 (2003).

\* cited by examiner

*Primary Examiner*—David J Steadman
*Assistant Examiner*—Jae W Lee
(74) *Attorney, Agent, or Firm*—Lando & Anastasi, LLP

(57) ABSTRACT

This invention relates to aggrecanase polypeptides and aggrecanase polypeptide/ligand complexes, crystals of aggrecanase and aggrecanase polypeptide/ligand complexes, and related methods and software systems.

25 Claims, 13 Drawing Sheets

213
|
PASLSRFVETLVVADDKMAAFHGAGLKRYLLTVMAAAAKAFKHPSIRNPV
SLVVTRLVILGSGEEGPQVGPSAAQTLRSFCAWQRGLNTPEDSDPDHFDT
AILFTRQDLCGVSTCDTLGMADVGTVCDPARSCAIVEDDGLQSAFTAAHQ
LGHVFNMLHDNSKPCISLNGPLSTSRHVMAPVMAHVDPEEPWSPCSARFI
TDPLDNGYGHCLLDKPEAPLHLPVTFPGKDYDADRQCQLTFGPDSRHCPQ
LPPPCAALWCSGHLNGHAMCQTKHSPWADGTPCGPAQACMGGRCLHMDQL
QDPNIPQA-DYKDDDDK(FLAG-tag)
          |
         520

(SEQ ID NO:1)

FIG. 1A

213
|
PASLSRFVETLVVADDKMAAFHGAGLKRYLLTVMAAAAKAFKHPSIRNPV
SLVVTRLVILGSGEEGPQVGPSAAQTLRSFCAWQRGLNTPEDSDPDHFDT
AILFTRQDLCGVSTCDTLGMADVGTVCDPARSCAIVEDDGLQSAFTAAHE
LGHVFNMLHDNSKPCISLNGPLSTSRHVMAPVMAHVDPEEPWSPCSARFI
TDPLDNGYGHCLLDKPEAPLHLPVTFPGKDYDADRQCQLTFGPDSRHCPQ
LPPPCAALWCSGHLNGHAMCQTKHSPWADGTPCGPAQACMGGRCLHMDQL
QDPNIPQA
        |
       520

(SEQ ID NO:2)

FIG. 1B

```
Agg2 Phe629strep

262  SISRARQVE  LLLVADASMA  RLYGRGLQHY  LLTLASIANR  LYSHASIENH
311  IRLAVVKVVV  LGDKDKSLEV  SKNAATTLKN  FCKWQHQHNQ  LGDDHEEHYD
361  AAILPTREDL  CGHHSCDTLG  MADVGTICSP  ERSCAVIEDD  GLMAAFTVAH
411  EIGHLLGLSH  DDSKPCEETP  GSTEDKRLMS  SILTSIDASK  PWSKCTSATI
461  TEFLDDGHGN  CLLDLPRKQI  LGPEELPGQT  YDATQQCNLT  FGPEYSVCPG
511  MDVCARLWCA  VVRQGQMVCL  TKKLPAVEGT  PCGKGRICLQ  GKCVDKTKKK
561  YYSTSSHGNW  GSWGSWGQCS  RSCGGGVQFA  YRHCNNPAPR  NNGRYCTGKR
611  AIYRSCSLMP  CPPNGKSF-GSAWSHPQFEK (Strep-tag)

SEQ ID NO:3
```

FIG. 3

SEQUENCE LISTING

<160> NUMBER OF SEQ ID NOS: 15

<210> SEQ ID NO 1
<211> LENGTH: 316
<212> TYPE: PRT
<213> ORGANISM: Homo sapiens

<400> SEQUENCE: 1

```
Phe Ala Ser Leu Ser Arg Phe Val Glu Thr Leu Val Val Ala Asp Asp
  1               5                  10                  15

Lys Met Ala Ala Phe His Gly Ala Gly Leu Lys Arg Tyr Leu Leu Thr
                 20                  25                  30

Val Met Ala Ala Ala Lys Ala Phe Lys His Pro Ser Ile Arg Asn
             35                  40                  45

Pro Val Ser Leu Val Val Thr Arg Leu Val Ile Leu Gly Ser Gly Glu
         50                  55                  60

Glu Gly Pro Gln Val Gly Pro Ser Ala Ala Gln Thr Leu Arg Ser Phe
 65                  70                  75                  80

Cys Ala Trp Gln Arg Gly Leu Asn Thr Pro Glu Asp Ser Asp Pro Asp
                 85                  90                  95

His Phe Asp Thr Ala Ile Leu Phe Thr Arg Gln Asp Leu Cys Gly Val
                100                 105                 110

Ser Thr Cys Asp Thr Leu Gly Met Ala Asp Val Gly Thr Val Cys Asp
            115                 120                 125

Pro Ala Arg Ser Cys Ala Ile Val Glu Asp Gly Leu Gln Ser Ala
        130                 135                 140

Phe Thr Ala Ala His Gln Leu Gly His Val Phe Asn Met Leu His Asp
145                 150                 155                 160

Asn Ser Lys Pro Cys Ile Ser Leu Asn Gly Pro Leu Ser Thr Ser Arg
                165                 170                 175

His Val Met Ala Pro Val Met Ala His Val Asp Pro Glu Glu Pro Trp
                180                 185                 190

Ser Pro Cys Ser Ala Arg Phe Ile Thr Asp Phe Leu Asp Asn Gly Tyr
                195                 200                 205

Gly His Cys Leu Leu Asp Lys Pro Glu Ala Pro Leu His Leu Pro Val
            210                 215                 220

Thr Phe Pro Gly Lys Asp Tyr Asp Ala Asp Arg Gln Cys Gln Leu Thr
225                 230                 235                 240

Phe Gly Pro Asp Ser Arg His Cys Pro Gln Leu Pro Pro Cys Ala
                245                 250                 255

Ala Leu Trp Cys Ser Gly His Leu Asn Gly His Ala Met Cys Gln Thr
            260                 265                 270

Lys His Ser Pro Trp Ala Asp Gly Thr Pro Cys Gly Pro Ala Gln Ala
        275                 280                 285

Cys Met Gly Gly Arg Cys Leu His Met Asp Gln Leu Gln Asp Phe Asn
    290                 295                 300

Ile Pro Gln Ala Asp Tyr Lys Asp Asp Asp Lys
305                 310                 315
```

<210> SEQ ID NO 2
<211> LENGTH: 308
<212> TYPE: PRT
<213> ORGANISM: Homo sapiens

<400> SEQUENCE: 2

```
Phe Ala Ser Leu Ser Arg Phe Val Glu Thr Leu Val Val Ala Asp Asp
 1               5                  10                  15

Lys Met Ala Ala Phe His Gly Ala Gly Leu Lys Arg Tyr Leu Leu Thr
            20                  25                  30

Val Met Ala Ala Ala Lys Ala Phe Lys His Pro Ser Ile Arg Asn
         35                  40                  45

Pro Val Ser Leu Val Val Thr Arg Leu Val Ile Leu Gly Ser Gly Glu
        50                  55                  60

Glu Gly Pro Gln Val Gly Pro Ser Ala Ala Gln Thr Leu Arg Ser Phe
 65              70                  75                  80

Cys Ala Trp Gln Arg Gly Leu Asn Thr Pro Glu Asp Ser Asp Pro Asp
                85                  90                  95

His Phe Asp Thr Ala Ile Leu Phe Thr Arg Gln Asp Leu Cys Gly Val
                100                 105                 110

Ser Thr Cys Asp Thr Leu Gly Met Ala Asp Val Gly Thr Val Cys Asp
            115                 120                 125

Pro Ala Arg Ser Cys Ala Ile Val Glu Asp Asp Gly Leu Gln Ser Ala
        130                 135                 140

Phe Thr Ala Ala His Glu Leu Gly His Val Phe Asn Met Leu His Asp
145                 150                 155                 160

Asn Ser Lys Pro Cys Ile Ser Leu Asn Gly Pro Leu Ser Thr Ser Arg
                165                 170                 175

His Val Met Ala Pro Val Met Ala His Val Asp Pro Glu Glu Pro Trp
            180                 185                 190

Ser Pro Cys Ser Ala Arg Phe Ile Thr Asp Phe Leu Asp Asn Gly Tyr
        195                 200                 205

Gly His Cys Leu Leu Asp Lys Pro Glu Ala Pro Leu His Leu Pro Val
        210                 215                 220

Thr Phe Pro Gly Lys Asp Tyr Asp Ala Asp Arg Gln Cys Gln Leu Thr
225                 230                 235                 240

Phe Gly Pro Asp Ser Arg His Cys Pro Gln Leu Pro Pro Cys Ala
                245                 250                 255

Ala Leu Trp Cys Ser Gly His Leu Asn Gly His Ala Met Cys Gln Thr
            260                 265                 270

Lys His Ser Pro Trp Ala Asp Gly Thr Pro Cys Gly Pro Ala Gln Ala
            275                 280                 285

Cys Met Gly Gly Arg Cys Leu His Met Asp Gln Leu Gln Asp Phe Asn
290                 295                 300

Ile Pro Gln Ala
305

<210> SEQ ID NO 3
<211> LENGTH: 378
<212> TYPE: PRT
<213> ORGANISM: Homo sapiens

<400> SEQUENCE: 3

Ser Ile Ser Arg Ala Arg Gln Val Glu Leu Leu Val Ala Asp Ala
 1               5                  10                  15

Ser Met Ala Arg Leu Tyr Gly Arg Gly Leu Gln His Tyr Leu Leu Thr
            20                  25                  30

Leu Ala Ser Ile Ala Asn Arg Leu Tyr Ser His Ala Ser Ile Glu Asn
            35                  40                  45

His Ile Arg Leu Ala Val Val Lys Val Val Val Leu Gly Asp Lys Asp
```

```
                50                      55                      60
Lys Ser Leu Glu Val Ser Lys Asn Ala Ala Thr Thr Leu Lys Asn Phe
 65                      70                      75                      80

Cys Lys Trp Gln His Gln His Asn Gln Leu Gly Asp Asp His Glu Glu
                         85                      90                      95

His Tyr Asp Ala Ala Ile Leu Phe Thr Arg Glu Asp Leu Cys Gly His
                        100                     105                     110

His Ser Cys Asp Thr Leu Gly Met Ala Asp Val Gly Thr Ile Cys Ser
                        115                     120                     125

Pro Glu Arg Ser Cys Ala Val Ile Glu Asp Gly Leu His Ala Ala
                130                     135                     140

Phe Thr Val Ala His Glu Ile Gly His Leu Leu Gly Leu Ser His Asp
145                     150                     155                     160

Asp Ser Lys Phe Cys Glu Glu Thr Phe Gly Ser Thr Glu Asp Lys Arg
                        165                     170                     175

Leu Met Ser Ser Ile Leu Thr Ser Ile Asp Ala Ser Lys Pro Trp Ser
                180                     185                     190

Lys Cys Thr Ser Ala Thr Ile Thr Glu Phe Leu Asp Asp Gly His Gly
                195                     200                     205

Asn Cys Leu Leu Asp Leu Pro Arg Lys Gln Ile Leu Gly Pro Glu Glu
        210                     215                     220

Leu Pro Gly Gln Thr Tyr Asp Ala Thr Gln Gln Cys Asn Leu Thr Phe
225                     230                     235                     240

Gly Pro Glu Tyr Ser Val Cys Pro Gly Met Asp Val Cys Ala Arg Leu
                        245                     250                     255

Trp Cys Ala Val Val Arg Gln Gly Gln Met Val Cys Leu Thr Lys Lys
                260                     265                     270

Leu Pro Ala Val Glu Gly Thr Pro Cys Gly Lys Gly Arg Ile Cys Leu
                275                     280                     285

Gln Gly Lys Cys Val Asp Lys Thr Lys Lys Tyr Tyr Ser Thr Ser
        290                     295                     300

Ser His Gly Asn Trp Gly Ser Trp Gly Ser Trp Gly Gln Cys Ser Arg
305                     310                     315                     320

Ser Cys Gly Gly Gly Val Gln Phe Ala Tyr Arg His Cys Asn Asn Pro
                        325                     330                     335

Ala Pro Arg Asn Asn Gly Arg Tyr Cys Thr Gly Lys Arg Ala Ile Tyr
                340                     345                     350

Arg Ser Cys Ser Leu Met Pro Cys Pro Pro Asn Gly Lys Ser Phe Gly
                355                     360                     365

Ser Ala Trp Ser His Pro Gln Phe Glu Lys
        370                     375

<210> SEQ ID NO 4
<211> LENGTH: 294
<212> TYPE: PRT
<213> ORGANISM: Homo sapiens

<400> SEQUENCE: 4

Ser Leu Ser Arg Phe Val Glu Thr Leu Val Val Ala Asp Asp Lys Met
 1               5                      10                      15

Ala Ala Phe His Gly Ala Gly Leu Lys Arg Tyr Leu Leu Thr Val Met
                 20                      25                      30

Ala Ala Ala Ala Lys Ala Phe Lys His Pro Ser Ile Arg Asn Pro Val
                 35                      40                      45
```

```
Ser Leu Val Val Thr Arg Leu Val Ile Leu Gly Ser Gly Glu Glu Gly
 50                  55                  60

Pro Gln Val Gly Pro Ser Ala Ala Gln Thr Leu Arg Ser Phe Cys Ala
 65                  70                  75                  80

Trp Gln Arg Gly Leu Asn Thr Pro Glu Asp Ser Asp Pro Asp His Phe
                 85                  90                  95

Asp Thr Ala Ile Leu Phe Thr Arg Gln Asp Leu Cys Gly Val Ser Thr
                100                 105                 110

Cys Asp Thr Leu Gly Met Ala Asp Val Gly Thr Val Cys Asp Pro Ala
            115                 120                 125

Arg Ser Cys Ala Ile Val Glu Asp Asp Gly Leu Gln Ser Ala Phe Thr
130                 135                 140

Ala Ala His Gln Leu Gly His Val Phe Asn Met Leu His Asp Asn Ser
145                 150                 155                 160

Lys Pro Cys Ile Ser Leu Asn Gly Pro Leu Ser Thr Ser Arg His Val
                165                 170                 175

Met Ala Pro Val Met Ala His Val Asp Pro Glu Glu Pro Trp Ser Pro
                180                 185                 190

Cys Ser Ala Arg Phe Ile Thr Asp Phe Leu Asp Asn Gly Tyr Gly His
            195                 200                 205

Cys Leu Leu Asp Lys Pro Glu Ala Pro Leu His Leu Pro Val Thr Phe
210                 215                 220

Pro Gly Lys Asp Tyr Asp Ala Asp Arg Gln Cys Gln Leu Thr Phe Gly
225                 230                 235                 240

Pro Asp Ser Arg His Cys Pro Gln Leu Pro Pro Cys Ala Ala Leu
                245                 250                 255

Trp Cys Ser Gly His Leu Asn Gly His Ala Met Cys Gln Thr Lys His
                260                 265                 270

Ser Pro Trp Ala Asp Gly Thr Pro Cys Gly Pro Ala Gln Ala Cys Met
            275                 280                 285

Gly Gly Arg Cys Leu His
            290

<210> SEQ ID NO 5
<211> LENGTH: 292
<212> TYPE: PRT
<213> ORGANISM: Homo sapiens

<400> SEQUENCE: 5

Leu Ser Arg Phe Val Glu Thr Leu Val Val Ala Asp Asp Lys Met Ala
  1               5                  10                  15

Ala Phe His Gly Ala Gly Leu Lys Arg Tyr Leu Leu Thr Val Met Ala
                 20                  25                  30

Ala Ala Ala Lys Ala Phe Lys His Pro Ser Ile Arg Asn Pro Val Ser
            35                  40                  45

Leu Val Val Thr Arg Leu Val Ile Leu Gly Ser Gly Glu Glu Gly Pro
 50                  55                  60

Gln Val Gly Pro Ser Ala Ala Gln Thr Leu Arg Ser Phe Cys Ala Trp
 65                  70                  75                  80

Gln Arg Gly Leu Asn Thr Pro Glu Asp Ser Asp Pro Asp His Phe Asp
                 85                  90                  95

Thr Ala Ile Leu Phe Thr Arg Gln Asp Leu Cys Gly Val Ser Thr Cys
                100                 105                 110

Asp Thr Leu Gly Met Ala Asp Val Gly Thr Val Cys Asp Pro Ala Arg
            115                 120                 125
```

```
Ser Cys Ala Ile Val Glu Asp Asp Gly Leu Gln Ser Ala Phe Thr Ala
    130                 135                 140

Ala His Gln Leu Gly His Val Phe Asn Met Leu His Asp Asn Ser Lys
145                 150                 155                 160

Pro Cys Ile Ser Leu Asn Gly Pro Leu Ser Thr Ser Arg His Val Met
                165                 170                 175

Ala Pro Val Met Ala His Val Asp Pro Glu Glu Pro Trp Ser Pro Cys
            180                 185                 190

Ser Ala Arg Phe Ile Thr Asp Phe Leu Asp Asn Gly Tyr Gly His Cys
        195                 200                 205

Leu Leu Asp Lys Pro Glu Ala Pro Leu His Leu Pro Val Thr Phe Pro
    210                 215                 220

Gly Lys Asp Tyr Asp Ala Asp Arg Gln Cys Gln Leu Thr Phe Gly Pro
225                 230                 235                 240

Asp Ser Arg His Cys Pro Gln Leu Pro Pro Cys Ala Ala Leu Trp
                245                 250                 255

Cys Ser Gly His Leu Asn Gly His Ala Met Cys Gln Thr Lys His Ser
                260                 265                 270

Pro Trp Ala Asp Gly Thr Pro Cys Gly Pro Ala Gln Ala Cys Met Gly
        275                 280                 285

Gly Arg Cys Leu
        290

<210> SEQ ID NO 6
<211> LENGTH: 293
<212> TYPE: PRT
<213> ORGANISM: Homo sapiens

<400> SEQUENCE: 6

Ser Leu Ser Arg Phe Val Glu Thr Leu Val Val Ala Asp Asp Lys Met
1               5                   10                  15

Ala Ala Phe His Gly Ala Gly Leu Lys Arg Tyr Leu Leu Thr Val Met
            20                  25                  30

Ala Ala Ala Lys Ala Phe Lys His Pro Ser Ile Arg Asn Pro Val
        35                  40                  45

Ser Leu Val Val Thr Arg Leu Val Ile Leu Gly Ser Gly Glu Glu Gly
    50                  55                  60

Pro Gln Val Gly Pro Ser Ala Ala Gln Thr Leu Arg Ser Phe Cys Ala
65                  70                  75                  80

Trp Gln Arg Gly Leu Asn Thr Pro Glu Asp Ser Asp Pro Asp His Phe
                85                  90                  95

Asp Thr Ala Ile Leu Phe Thr Arg Gln Asp Leu Cys Gly Val Ser Thr
            100                 105                 110

Cys Asp Thr Leu Gly Met Ala Asp Val Gly Thr Val Cys Asp Pro Ala
        115                 120                 125

Arg Ser Cys Ala Ile Val Glu Asp Asp Gly Leu Gln Ser Ala Phe Thr
    130                 135                 140

Ala Ala His Gln Leu Gly His Val Phe Asn Met Leu His Asp Asn Ser
145                 150                 155                 160

Lys Pro Cys Ile Ser Leu Asn Gly Pro Leu Ser Thr Ser Arg His Val
                165                 170                 175

Met Ala Pro Val Met Ala His Val Asp Pro Glu Glu Pro Trp Ser Pro
            180                 185                 190

Cys Ser Ala Arg Phe Ile Thr Asp Phe Leu Asp Asn Gly Tyr Gly His
```

```
                  195                 200                 205
Cys Leu Leu Asp Lys Pro Glu Ala Pro Leu His Leu Pro Val Thr Phe
    210                 215                 220

Pro Gly Lys Asp Tyr Asp Ala Asp Arg Gln Cys Gln Leu Thr Phe Gly
225                 230                 235                 240

Pro Asp Ser Arg His Cys Pro Gln Leu Pro Pro Cys Ala Ala Leu
                245                 250                 255

Trp Cys Ser Gly His Leu Asn Gly His Ala Met Cys Gln Thr Lys His
                260                 265                 270

Ser Pro Trp Ala Asp Gly Thr Pro Cys Gly Pro Ala Gln Ala Cys Met
                275                 280                 285

Gly Gly Arg Cys Leu
            290

<210> SEQ ID NO 7
<211> LENGTH: 292
<212> TYPE: PRT
<213> ORGANISM: Homo sapiens

<400> SEQUENCE: 7

Arg Phe Val Glu Thr Leu Val Val Ala Asp Asp Lys Met Ala Ala Phe
1               5                   10                  15

His Gly Ala Gly Leu Lys Arg Tyr Leu Leu Thr Val Met Ala Ala Ala
                20                  25                  30

Ala Lys Ala Phe Lys His Pro Ser Ile Arg Asn Pro Val Ser Leu Val
            35                  40                  45

Val Thr Arg Leu Val Ile Leu Gly Ser Gly Glu Glu Gly Pro Gln Val
    50                  55                  60

Gly Pro Ser Ala Ala Gln Thr Leu Arg Ser Phe Cys Ala Trp Gln Arg
65                  70                  75                  80

Gly Leu Asn Thr Pro Glu Asp Ser Asp Pro Asp His Phe Asp Thr Ala
                85                  90                  95

Ile Leu Phe Thr Arg Gln Asp Leu Cys Gly Val Ser Thr Cys Asp Thr
            100                 105                 110

Leu Gly Met Ala Asp Val Gly Thr Val Cys Asp Pro Ala Arg Ser Cys
        115                 120                 125

Ala Ile Val Glu Asp Asp Gly Leu Gln Ser Ala Phe Thr Ala Ala His
    130                 135                 140

Gln Leu Gly His Val Phe Asn Met Leu His Asp Asn Ser Lys Pro Cys
145                 150                 155                 160

Ile Ser Leu Asn Gly Pro Leu Ser Thr Ser Arg His Val Met Ala Pro
                165                 170                 175

Val Met Ala His Val Asp Pro Glu Glu Pro Trp Ser Pro Cys Ser Ala
            180                 185                 190

Arg Phe Ile Thr Asp Phe Leu Asp Asn Gly Tyr Gly His Cys Leu Leu
        195                 200                 205

Asp Lys Pro Glu Ala Pro Leu His Leu Pro Val Thr Phe Pro Gly Lys
    210                 215                 220

Asp Tyr Asp Ala Asp Arg Gln Cys Gln Leu Thr Phe Gly Pro Asp Ser
225                 230                 235                 240

Arg His Cys Pro Gln Leu Pro Pro Cys Ala Ala Leu Trp Cys Ser
                245                 250                 255

Gly His Leu Asn Gly His Ala Met Cys Gln Thr Lys His Ser Pro Trp
            260                 265                 270
```

```
Ala Asp Gly Thr Pro Cys Gly Pro Ala Gln Ala Cys Met Gly Gly Arg
        275                 280                 285

Cys Leu His Met
        290

<210> SEQ ID NO 8
<211> LENGTH: 292
<212> TYPE: PRT
<213> ORGANISM: Homo sapiens

<400> SEQUENCE: 8

Ser Arg Phe Val Glu Thr Leu Val Val Ala Asp Asp Lys Met Ala Ala
  1               5                  10                  15

Phe His Gly Ala Gly Leu Lys Arg Tyr Leu Leu Thr Val Met Ala Ala
             20                  25                  30

Ala Ala Lys Ala Phe Lys His Pro Ser Ile Arg Asn Pro Val Ser Leu
         35                  40                  45

Val Val Thr Arg Leu Val Ile Leu Gly Ser Gly Glu Glu Gly Pro Gln
     50                  55                  60

Val Gly Pro Ser Ala Ala Gln Thr Leu Arg Ser Phe Cys Ala Trp Gln
 65                  70                  75                  80

Arg Gly Leu Asn Thr Pro Glu Asp Ser Asp Pro Asp His Phe Asp Thr
                 85                  90                  95

Ala Ile Leu Phe Thr Arg Gln Asp Leu Cys Gly Val Ser Thr Cys Asp
            100                 105                 110

Thr Leu Gly Met Ala Asp Val Gly Thr Val Cys Asp Pro Ala Arg Ser
        115                 120                 125

Cys Ala Ile Val Glu Asp Gly Leu Gln Ser Ala Phe Thr Ala Ala
    130                 135                 140

His Gln Leu Gly His Val Phe Asn Met Leu His Asp Asn Ser Lys Pro
145                 150                 155                 160

Cys Ile Ser Leu Asn Gly Pro Leu Ser Thr Ser Arg His Val Met Ala
                165                 170                 175

Pro Val Met Ala His Val Asp Pro Glu Glu Pro Trp Ser Pro Cys Ser
            180                 185                 190

Ala Arg Phe Ile Thr Asp Phe Leu Asp Asn Gly Tyr Gly His Cys Leu
        195                 200                 205

Leu Asp Lys Pro Glu Ala Pro Leu His Leu Pro Val Thr Phe Pro Gly
    210                 215                 220

Lys Asp Tyr Asp Ala Asp Arg Gln Cys Gln Leu Thr Phe Gly Pro Asp
225                 230                 235                 240

Ser Arg His Cys Pro Gln Leu Pro Pro Cys Ala Ala Leu Trp Cys
                245                 250                 255

Ser Gly His Leu Asn Gly His Ala Met Cys Gln Thr Lys His Ser Pro
            260                 265                 270

Trp Ala Asp Gly Thr Pro Cys Gly Pro Ala Gln Ala Cys Met Gly Gly
        275                 280                 285

Arg Cys Leu His
        290

<210> SEQ ID NO 9
<211> LENGTH: 296
<212> TYPE: PRT
<213> ORGANISM: Homo sapiens

<400> SEQUENCE: 9
```

-continued

```
Ala Ser Leu Ser Arg Phe Val Glu Thr Leu Val Val Ala Asp Asp Lys
 1               5                  10                  15

Met Ala Ala Phe His Gly Ala Gly Leu Lys Arg Tyr Leu Leu Thr Val
             20                  25                  30

Met Ala Ala Ala Lys Ala Phe Lys His Pro Ser Ile Arg Asn Pro
         35                  40                  45

Val Ser Leu Val Val Thr Arg Leu Val Ile Leu Gly Ser Gly Glu Glu
 50                  55                  60

Gly Pro Gln Val Gly Pro Ser Ala Ala Gln Thr Leu Arg Ser Phe Cys
 65                  70                  75                  80

Ala Trp Gln Arg Gly Leu Asn Thr Pro Glu Asp Ser Asp Pro Asp His
                 85                  90                  95

Phe Asp Thr Ala Ile Leu Phe Thr Arg Gln Asp Leu Cys Gly Val Ser
             100                 105                 110

Thr Cys Asp Thr Leu Gly Met Ala Asp Val Gly Thr Val Cys Asp Pro
         115                 120                 125

Ala Arg Ser Cys Ala Ile Val Glu Asp Gly Leu Gln Ser Ala Phe
         130                 135                 140

Thr Ala Ala His Gln Leu Gly His Val Phe Asn Met Leu His Asp Asn
145                 150                 155                 160

Ser Lys Pro Cys Ile Ser Leu Asn Gly Pro Leu Ser Thr Ser Arg His
                 165                 170                 175

Val Met Ala Pro Val Met Ala His Val Asp Pro Glu Glu Pro Trp Ser
             180                 185                 190

Pro Cys Ser Ala Arg Phe Ile Thr Asp Phe Leu Asp Asn Gly Tyr Gly
         195                 200                 205

His Cys Leu Leu Asp Lys Pro Glu Ala Pro Leu His Leu Pro Val Thr
 210                 215                 220

Phe Pro Gly Lys Asp Tyr Asp Ala Asp Arg Gln Cys Gln Leu Thr Phe
225                 230                 235                 240

Gly Pro Asp Ser Arg His Cys Pro Gln Leu Pro Pro Cys Ala Ala
                 245                 250                 255

Leu Trp Cys Ser Gly His Leu Asn Gly His Ala Met Cys Gln Thr Lys
                 260                 265                 270

His Ser Pro Trp Ala Asp Gly Thr Pro Cys Gly Pro Ala Gln Ala Cys
                 275                 280                 285

Met Gly Gly Arg Cys Leu His Met
             290                 295
```

<210> SEQ ID NO 10
<211> LENGTH: 296
<212> TYPE: PRT
<213> ORGANISM: Homo sapiens

<400> SEQUENCE: 10

```
Ala Ala Ser Leu Ser Arg Phe Val Glu Thr Leu Val Val Ala Asp Asp
 1               5                  10                  15

Lys Met Ala Ala Phe His Gly Ala Gly Leu Lys Arg Tyr Leu Leu Thr
             20                  25                  30

Val Met Ala Ala Ala Lys Ala Phe Lys His Pro Ser Ile Arg Asn
         35                  40                  45

Pro Val Ser Leu Val Val Thr Arg Leu Val Ile Leu Gly Ser Gly Glu
 50                  55                  60

Glu Gly Pro Gln Val Gly Pro Ser Ala Ala Gln Thr Leu Arg Ser Phe
 65                  70                  75                  80
```

```
Cys Ala Trp Gln Arg Gly Leu Asn Thr Pro Glu Asp Ser Asp Pro Asp
                 85                  90                  95

His Phe Asp Thr Ala Ile Leu Phe Thr Arg Gln Asp Leu Cys Gly Val
            100                 105                 110

Ser Thr Cys Asp Thr Leu Gly Met Ala Asp Val Gly Thr Val Cys Asp
        115                 120                 125

Pro Ala Arg Ser Cys Ala Ile Val Glu Asp Asp Gly Leu Gln Ser Ala
    130                 135                 140

Phe Thr Ala Ala His Gln Leu Gly His Val Phe Asn Met Leu His Asp
145                 150                 155                 160

Asn Ser Lys Pro Cys Ile Ser Leu Asn Gly Pro Leu Ser Thr Ser Arg
                165                 170                 175

His Val Met Ala Pro Val Met Ala His Val Asp Pro Glu Glu Pro Trp
            180                 185                 190

Ser Pro Cys Ser Ala Arg Phe Ile Thr Asp Phe Leu Asp Asn Gly Tyr
        195                 200                 205

Gly His Cys Leu Leu Asp Lys Pro Glu Ala Pro Leu His Leu Pro Val
    210                 215                 220

Thr Phe Pro Gly Lys Asp Tyr Asp Ala Asp Arg Gln Cys Gln Leu Thr
225                 230                 235                 240

Phe Gly Pro Asp Ser Arg His Cys Pro Gln Leu Pro Pro Pro Cys Ala
                245                 250                 255

Ala Leu Trp Cys Ser Gly His Leu Asn Gly His Ala Met Cys Gln Thr
            260                 265                 270

Lys His Ser Pro Trp Ala Asp Gly Thr Pro Cys Gly Pro Ala Gln Ala
        275                 280                 285

Cys Met Gly Gly Arg Cys Leu His
    290                 295

<210> SEQ ID NO 11
<211> LENGTH: 293
<212> TYPE: PRT
<213> ORGANISM: Homo sapiens

<400> SEQUENCE: 11

Leu Ser Arg Phe Val Glu Thr Leu Val Val Ala Asp Asp Lys Met Ala
 1               5                  10                  15

Ala Phe His Gly Ala Gly Leu Lys Arg Tyr Leu Leu Thr Val Met Ala
            20                  25                  30

Ala Ala Ala Lys Ala Phe Lys His Pro Ser Ile Arg Asn Pro Val Ser
        35                  40                  45

Leu Val Val Thr Arg Leu Val Ile Leu Gly Ser Gly Glu Glu Gly Pro
    50                  55                  60

Gln Val Gly Pro Ser Ala Ala Gln Thr Leu Arg Ser Phe Cys Ala Trp
65                  70                  75                  80

Gln Arg Gly Leu Asn Thr Pro Glu Asp Ser Asp Pro Asp His Phe Asp
                85                  90                  95

Thr Ala Ile Leu Phe Thr Arg Gln Asp Leu Cys Gly Val Ser Thr Cys
            100                 105                 110

Asp Thr Leu Gly Met Ala Asp Val Gly Thr Val Cys Asp Pro Ala Arg
        115                 120                 125

Ser Cys Ala Ile Val Glu Asp Asp Gly Leu Gln Ser Ala Phe Thr Ala
    130                 135                 140

Ala His Gln Leu Gly His Val Phe Asn Met Leu His Asp Asn Ser Lys
```

```
145                 150                 155                 160

Pro Cys Ile Ser Leu Asn Gly Pro Leu Ser Thr Ser Arg His Val Met
            165                 170                 175

Ala Pro Val Met Ala His Val Asp Pro Glu Glu Pro Trp Ser Pro Cys
            180                 185                 190

Ser Ala Arg Phe Ile Thr Asp Phe Leu Asp Asn Gly Tyr Gly His Cys
            195                 200                 205

Leu Leu Asp Lys Pro Glu Ala Pro Leu His Leu Pro Val Thr Phe Pro
    210                 215                 220

Gly Lys Asp Tyr Asp Ala Asp Arg Gln Cys Gln Leu Thr Phe Gly Pro
225                 230                 235                 240

Asp Ser Arg His Cys Pro Gln Leu Pro Pro Cys Ala Ala Leu Trp
            245                 250                 255

Cys Ser Gly His Leu Asn Gly His Ala Met Cys Gln Thr Lys His Ser
            260                 265                 270

Pro Trp Ala Asp Gly Thr Pro Cys Gly Pro Ala Gln Ala Cys Met Gly
            275                 280                 285

Gly Arg Cys Leu His
    290

<210> SEQ ID NO 12
<211> LENGTH: 291
<212> TYPE: PRT
<213> ORGANISM: Homo sapiens

<400> SEQUENCE: 12

Leu Ser Arg Phe Val Glu Thr Leu Val Val Ala Asp Asp Lys Met Ala
1               5                   10                  15

Ala Phe His Gly Ala Gly Leu Lys Arg Tyr Leu Leu Thr Val Met Ala
            20                  25                  30

Ala Ala Ala Lys Ala Phe Lys His Pro Ser Ile Arg Asn Pro Val Ser
        35                  40                  45

Leu Val Val Thr Arg Leu Val Ile Leu Gly Ser Gly Glu Glu Gly Pro
    50                  55                  60

Gln Val Gly Pro Ser Ala Ala Gln Thr Leu Arg Ser Phe Cys Ala Trp
65                  70                  75                  80

Gln Arg Gly Leu Asn Thr Pro Glu Asp Ser Asp Pro Asp His Phe Asp
            85                  90                  95

Thr Ala Ile Leu Phe Thr Arg Gln Asp Leu Cys Gly Val Ser Thr Cys
            100                 105                 110

Asp Thr Leu Gly Met Ala Asp Val Gly Thr Val Cys Asp Pro Ala Arg
        115                 120                 125

Ser Cys Ala Ile Val Glu Asp Asp Gly Leu Gln Ser Ala Phe Thr Ala
    130                 135                 140

Ala His Gln Leu Gly His Val Phe Asn Met Leu His Asp Asn Ser Lys
145                 150                 155                 160

Pro Cys Ile Ser Leu Asn Gly Pro Leu Ser Thr Ser Arg His Val Met
            165                 170                 175

Ala Pro Val Met Ala His Val Asp Pro Glu Glu Pro Trp Ser Pro Cys
            180                 185                 190

Ser Ala Arg Phe Ile Thr Asp Phe Leu Asp Asn Gly Tyr Gly His Cys
            195                 200                 205

Leu Leu Asp Lys Pro Glu Ala Pro Leu His Leu Pro Val Thr Phe Pro
    210                 215                 220
```

```
Gly Lys Asp Tyr Asp Ala Asp Arg Gln Cys Gln Leu Thr Phe Gly Pro
225                 230                 235                 240

Asp Ser Arg His Cys Pro Gln Leu Pro Pro Pro Cys Ala Ala Leu Trp
            245                 250                 255

Cys Ser Gly His Leu Asn Gly His Ala Met Cys Gln Thr Lys His Ser
            260                 265                 270

Pro Trp Ala Asp Gly Thr Pro Cys Gly Pro Ala Gln Ala Cys Met Gly
            275                 280                 285

Gly Arg Cys
        290

<210> SEQ ID NO 13
<211> LENGTH: 290
<212> TYPE: PRT
<213> ORGANISM: Homo sapiens

<400> SEQUENCE: 13

Ala Arg Gln Val Glu Leu Leu Val Ala Asp Ala Ser Met Ala Arg
  1               5                  10                  15

Leu Tyr Gly Arg Gly Leu Gln His Tyr Leu Leu Thr Leu Ala Ser Ile
            20                  25                  30

Ala Asn Arg Leu Tyr Ser His Ala Ser Ile Glu Asn His Ile Arg Leu
            35                  40                  45

Ala Val Val Lys Val Val Leu Gly Asp Lys Asp Lys Ser Leu Glu
 50                  55                  60

Val Ser Lys Asn Ala Ala Thr Thr Leu Lys Asn Phe Cys Lys Trp Gln
 65                  70                  75                  80

His Gln His Asn Gln Leu Gly Asp Asp His Glu Glu His Tyr Asp Ala
            85                  90                  95

Ala Ile Leu Phe Thr Arg Glu Asp Leu Cys Gly His His Ser Cys Asp
            100                 105                 110

Thr Leu Gly Met Ala Asp Val Gly Thr Ile Cys Ser Pro Glu Arg Ser
            115                 120                 125

Cys Ala Val Ile Glu Asp Asp Gly Leu His Ala Ala Phe Thr Val Ala
 130                 135                 140

His Glu Ile Gly His Leu Leu Gly Leu Ser His Asp Asp Ser Lys Phe
145                 150                 155                 160

Cys Glu Glu Thr Phe Gly Ser Thr Glu Asp Lys Arg Leu Met Ser Ser
            165                 170                 175

Ile Leu Thr Ser Ile Asp Ala Ser Lys Pro Trp Ser Lys Cys Thr Ser
            180                 185                 190

Ala Thr Ile Thr Glu Phe Leu Asp Asp Gly His Gly Asn Cys Leu Leu
            195                 200                 205

Asp Leu Pro Arg Lys Gln Ile Leu Gly Pro Glu Glu Leu Pro Gly Gln
 210                 215                 220

Thr Tyr Asp Ala Thr Gln Gln Cys Asn Leu Thr Phe Gly Pro Glu Tyr
225                 230                 235                 240

Ser Val Cys Pro Gly Met Asp Val Cys Ala Arg Leu Trp Cys Ala Val
            245                 250                 255

Val Arg Gln Gly Gln Met Val Cys Leu Thr Lys Lys Leu Pro Ala Val
            260                 265                 270

Glu Gly Thr Pro Cys Gly Lys Gly Arg Ile Cys Leu Gln Gly Lys Cys
            275                 280                 285

Val Asp
    290
```

<210> SEQ ID NO 14
<211> LENGTH: 292
<212> TYPE: PRT
<213> ORGANISM: Homo sapiens

<400> SEQUENCE: 14

```
Arg Ala Arg Gln Val Glu Leu Leu Val Ala Asp Ala Ser Met Ala
 1               5                  10                  15

Arg Leu Tyr Gly Arg Gly Leu Gln His Tyr Leu Leu Thr Leu Ala Ser
             20                  25                  30

Ile Ala Asn Arg Leu Tyr Ser His Ala Ser Ile Glu Asn His Ile Arg
         35                  40                  45

Leu Ala Val Val Lys Val Val Leu Gly Asp Lys Asp Lys Ser Leu
 50                  55                  60

Glu Val Ser Lys Asn Ala Ala Thr Thr Leu Lys Asn Phe Cys Lys Trp
 65                  70                  75                  80

Gln His Gln His Asn Gln Leu Gly Asp Asp His Glu His Tyr Asp
             85                  90                  95

Ala Ala Ile Leu Phe Thr Arg Glu Asp Leu Cys Gly His His Ser Cys
                100                 105                 110

Asp Thr Leu Gly Met Ala Asp Val Gly Thr Ile Cys Ser Pro Glu Arg
            115                 120                 125

Ser Cys Ala Val Ile Glu Asp Asp Gly Leu His Ala Ala Phe Thr Val
130                 135                 140

Ala His Glu Ile Gly His Leu Leu Gly Leu Ser His Asp Ser Lys
145                 150                 155                 160

Phe Cys Glu Glu Thr Phe Gly Ser Thr Glu Asp Lys Arg Leu Met Ser
                165                 170                 175

Ser Ile Leu Thr Ser Ile Asp Ala Ser Lys Pro Trp Ser Lys Cys Thr
            180                 185                 190

Ser Ala Thr Ile Thr Glu Phe Leu Asp Asp Gly His Gly Asn Cys Leu
        195                 200                 205

Leu Asp Leu Pro Arg Lys Gln Ile Leu Gly Pro Glu Glu Leu Pro Gly
210                 215                 220

Gln Thr Tyr Asp Ala Thr Gln Gln Cys Asn Leu Thr Phe Gly Pro Glu
225                 230                 235                 240

Tyr Ser Val Cys Pro Gly Met Asp Val Cys Ala Arg Leu Trp Cys Ala
                245                 250                 255

Val Val Arg Gln Gly Gln Met Val Cys Leu Thr Lys Lys Leu Pro Ala
            260                 265                 270

Val Glu Gly Thr Pro Cys Gly Lys Gly Arg Ile Cys Leu Gln Gly Lys
        275                 280                 285

Cys Val Asp Lys
    290
```

<210> SEQ ID NO 15
<211> LENGTH: 9
<212> TYPE: PRT
<213> ORGANISM: Artificial Sequence
<220> FEATURE:
<223> OTHER INFORMATION: Synthetically generated peptide

<400> SEQUENCE: 15

```
Thr Glu Gly Ala Arg Gly Ser Val Ile
 1               5
```

AGGRECANASE STRUCTURE

RELATED APPLICATIONS

This application claims the benefit of U.S. Provisional Application No. 60/711,457, filed Aug. 25, 2005, which is incorporated herein by reference in its entirety.

TECHNICAL FIELD

This invention relates to aggrecanase polypeptides, aggrecanase polypeptide/ligand complexes, crystals of aggrecanase polypeptides, crystals of aggrecanase polypeptide/ligand complexes, and related methods and software systems.

BACKGROUND

Aggrecanases are enzymes that can cleave cartilage aggrecan, a component of the extracellular matrix. Cartilage aggrecan generally includes a core protein with multiple functional domains that allow the cartilage to resist compressive forces. When the degradation of extracellular matrix components exceeds the synthesis of extracellular matrix components, there is a loss of aggrecan and a subsequent disruption of cartilage, resulting in a disruption of the structure and function of certain tissue types. The degradation of aggrecan is believed to be pathophysiological event that is seen in the earlier stages of joint diseases such as osteoarthritis (OA) and rheumatoid arthritis.

SUMMARY

In one aspect, the invention features a crystallized polypeptide-ligand complex that includes an aggrecanase-2 polypeptide and a ligand.

In another aspect the invention features a crystallized polypeptide-ligand complex that includes an aggrecanase-2 polypeptide and a peptidomimetic ligand having a metal chelating moiety.

In yet another aspect, the invention features a composition that includes a crystal, which includes an aggrecanase-2 polypeptide and a ligand.

In another aspect, the invention features a method that includes using a three-dimensional model of a complex to design an agent that binds the aggrecanase-2 polypeptide. The complex includes an aggrecanase-2 polypeptide bound to a ligand.

In a further aspect, the invention features a method to design an agent that binds the aggrecanase-2 polypeptide. The method includes using a three-dimensional model of an aggrecanase-2 polypeptide In another aspect, the invention features a method of selecting an agent by performing rational drug design with a three-dimensional structure of a crystalline complex that includes an aggrecanase-2 polypeptide. The agent is contacted with an aggrecanase-2 polypeptide, and an ability of the agent to bind the aggrecanase-2 polypeptide is detected.

In another aspect, the invention features a method that includes contacting an aggrecanase-2 polypeptide with a ligand to form a composition and crystallizing the composition to form a crystalline complex in which the ligand is bound to the aggrecanase-2 polypeptide. The crystalline complex can diffract X-rays to a resolution of at least about 3.5 Å.

In another aspect, the invention features a software system that includes instructions for causing a computer system to accept information relating to the structure of an aggrecanase-2 polypeptide bound to a ligand. The instructions further cause a computer system to accept information relating to a candidate agent, and determine binding characteristics of the candidate agent to the aggrecanase-2 polypeptide. The determination is based on the information relating to the structure of the aggrecanase-2 polypeptide bound to the ligand and to the information relating to the candidate agent.

In a further aspect, the invention features a computer program residing on a computer readable medium on which is stored a plurality of instructions. When the instructions are executed by one or more processors, the processors accept information relating to the structure of a complex that includes an aggrecanase-2 polypeptide bound to a ligand. The processors further accept information relating to a candidate agent and determine binding characteristics of the candidate agent to the aggrecanase-2 polypeptide. Such determination is based on the information relating to the structure of the aggrecanase-2 polypeptide and to the information relating to the candidate agent.

In another aspect, the invention features a method that includes accepting information relating to the structure of a complex including an aggrecanase-2 polypeptide bound to a ligand. The method further includes modeling the binding characteristics of the aggrecanase-2 polypeptide with a candidate agent. Such a method is implemented by a software system.

In another aspect, the invention features a computer program residing on a computer readable medium on which is stored a plurality of instructions. When the instructions are executed by one or more processors, the processors accept information relating to a structure of a complex that includes an aggrecanase-2 polypeptide bound to a ligand and model the binding characteristics of the aggrecanase-2 polypeptide with a candidate agent.

In another aspect, the invention features a software system that includes instructions for causing a computer system to accept information relating to a structure of a complex including an aggrecanase-2 polypeptide bound to a ligand. The instructions further cause the computer system to model the binding characteristics of the aggrecanase-2 polypeptide with a candidate agent.

In another aspect, the invention features a method of modulating aggrecanase-2 activity in a subject. The method includes using rational drug design to select an agent capable of modulating aggrecanase-2 activity and administering a therapeutically effective amount of the agent to the subject.

In another aspect, the invention features a method of treating a subject having a condition associated with aggrecanase-2 activity. The method includes using rational drug design to select an agent that is capable of affecting aggrecanase-2 activity and administering a therapeutically effective amount of the agent to a subject in need of such an agent.

In yet another aspect, the invention features a method of prophylactically treating a subject susceptible to a condition associated with aggrecanase-2 activity. The method includes determining that the subject is susceptible to the condition, using rational drug design to select an agent that is capable of effecting aggrecanase-2 activity, and administering a therapeutically effective amount of the agent to the subject.

Other features and advantages of the invention will be apparent from the description, drawings and claims.

DESCRIPTION OF DRAWINGS

FIG. 1A is the amino acid sequence (SEQ ID NO:1) of a fragment of a human Agg-1 polypeptide (Agg-1-A1C2) that includes the catalytic domain (amino acids 214-428) and the disintegrin-like domain (amino acids 437-509) and a mutation at amino acid 362 (Glu362Gln) that makes the polypeptide more amenable to crystallization. The glutamine at position 362 is indicated in bold and underlined. A FLAG-Tag (indicated in bold) fused to the C-terminus of the polypeptide facilitated purification.

FIG. 1B is the wildtype amino acid sequence (SEQ ID NO:2) of a fragment of a human Agg-1 polypeptide corresponding to the mutant FLAG-tagged fragment described in FIG. 1A. The wildtype sequence includes the catalytic domain (amino acids 214-428) and the disintegrin-like domain (amino acids 437-509). The wildtype glutamate at position 362 is indicated in bold and underlined.

FIG. 3 is the amino acid sequence (SEQ ID NO:3) of a fragment of a human Agg-2 polypeptide including the catalytic domain (amino acids 265-476), disintegrin-like domain (amino acids 486-556), and thrombospondin-like domain (amino acids 557-628). A strep-tag is fused to the C-terminus of the polypeptide and is indicated in bold.

Like reference symbols in the various drawings indicate like elements.

DETAILED DESCRIPTION

In general, this invention relates to aggrecanase polypeptides, aggrecanase polypeptide/ligand complexes, crystals of aggrecanase polypeptides, crystals of aggrecanase polypeptide/ligand complexes, and related methods and software systems. Without wishing to be bound by theory, it is believed that crystal structures of aggrecanase polypeptides and/or aggrecanase polypeptide/ligand complexes can be useful for designing or identifying other ligands that can interact with aggrecanase polypeptides.

As an example, Agg-1 and Agg-2 aggrecanases can cleave between Glu373 and Ala374 of aggrecan, and aggrecan fragments resulting from such cleavage have been predominantly found in synovial fluids of patients with osteoarthritis and joint injury. Therefore, it is believed that identification of aggrecanase inhibitors may be useful for treatment of these disorders.

Figure 2:
FIG. 2 is a ribbon diagram illustrating the structure of the Agg-1-A1C2 polypeptide. Calcium atoms and zinc atoms are also indicated.

An exemplary aggrecanase polypeptide is a human Agg-1 polypeptide. FIG. 1A is the amino acid sequence (SEQ ID NO:1) of a fragment of a human Agg-1 polypeptide (Agg-1-A1C2) that includes the catalytic domain (amino acids 214-428) and the disintegrin-like domain (amino acids 437-509) and a mutation at amino acid 362 (Glu362Gln) that makes the polypeptide more amenable to crystallization. The glutamine at position 362 is indicated in bold and underlined. A FLAG-Tag (indicated in bold) fused to the C-terminus of the polypeptide facilitated purification. FIG. 1B is the wildtype amino acid sequence (SEQ ID NO:2) of a fragment of a human Agg-1 polypeptide corresponding to the mutant FLAG-tagged fragment described in FIG. 1A. The wildtype sequence includes the catalytic domain (amino acids 214-428) and the disintegrin-like domain (amino acids 437-509). The wildtype glutamate at position 362 is indicated in bold and underlined. FIG. 2 is a ribbon diagram illustrating the structure of the Agg-1-A1C2 polypeptide (Calcium atoms and zinc atoms are also indicated). The coordinates of the crystal structure of the Agg-1-A1C2 polypeptide are provided below at Table 4.

Another exemplary aggrecanase polypeptide is a human Agg-2 polypeptide. FIG. 3 is the amino acid sequence (SEQ ID NO:3) of a fragment of a human Agg-2 polypeptide including the catalytic domain (amino acids 265-476), disintegrin-like domain (amino acids 486-556), and thrombospondin-like domain (amino acids 557-628).

Figure 4:
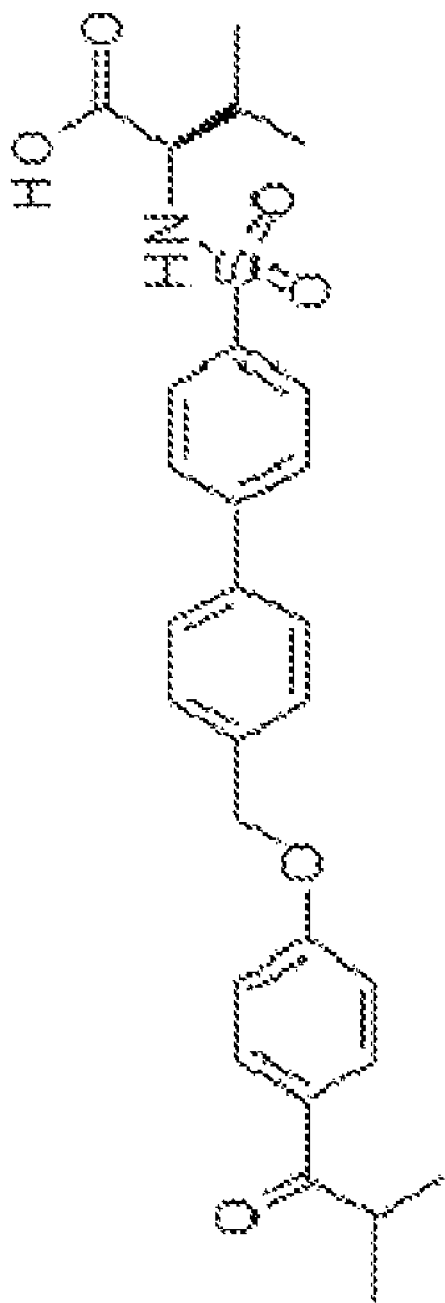
FIG. 4 is the chemical structure of 2-[4'-(4-Isobutyryl-phenoxymethyl)-biphenyl-4-sulfonylamino]-3-methyl-butyric acid (Compound 1).
Figure 5:
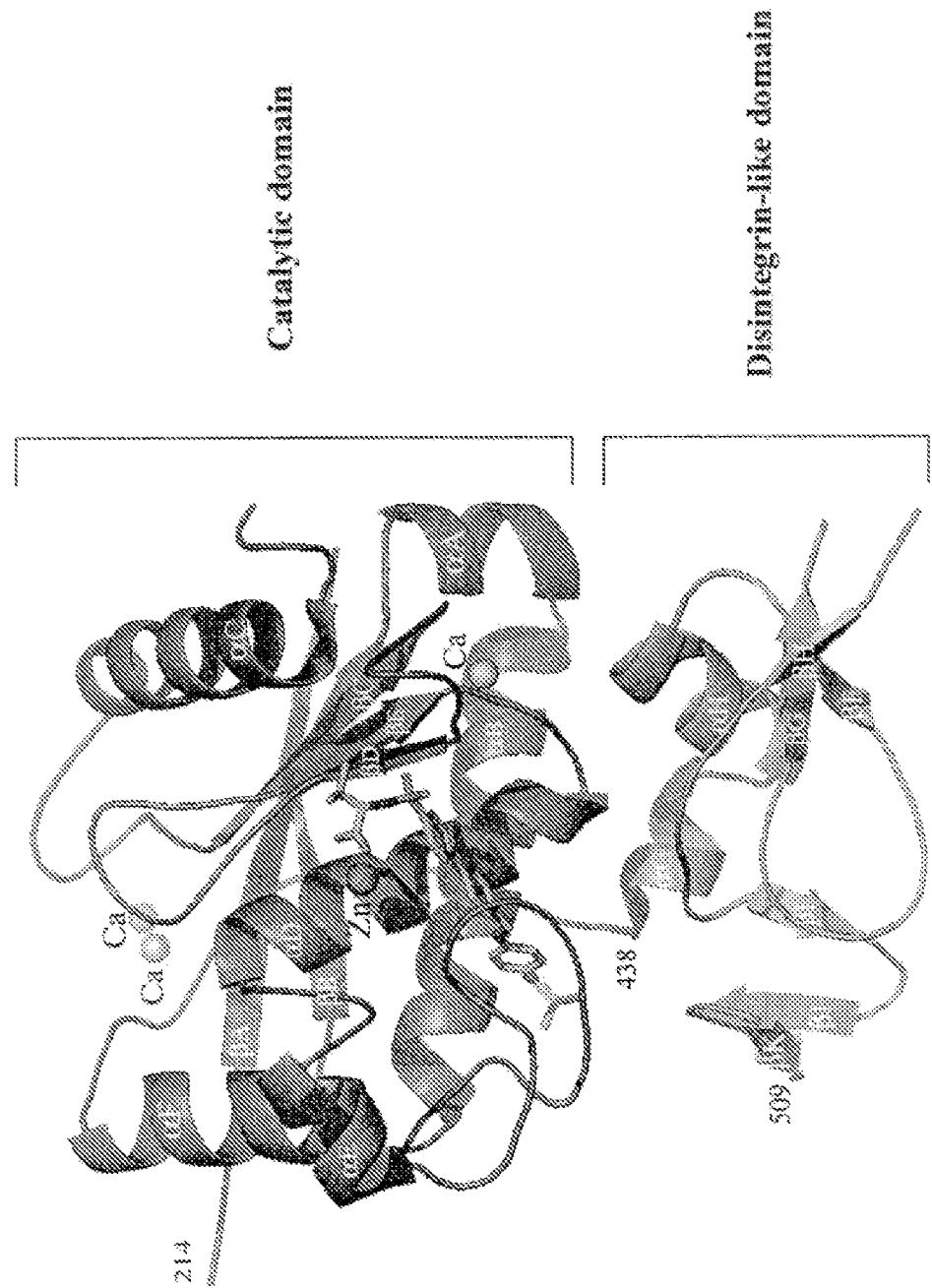
FIG. 5 is a ribbon diagram illustrating the structure of the human Agg-1-A1C2 polypeptide bound to the inhibitor Compound 1. Structural helices are identified by "αA" through "αH." Structural sheets are indicated by "βA" through "βK." Calcium atoms and zinc atoms are also indicated.
Figure 6:
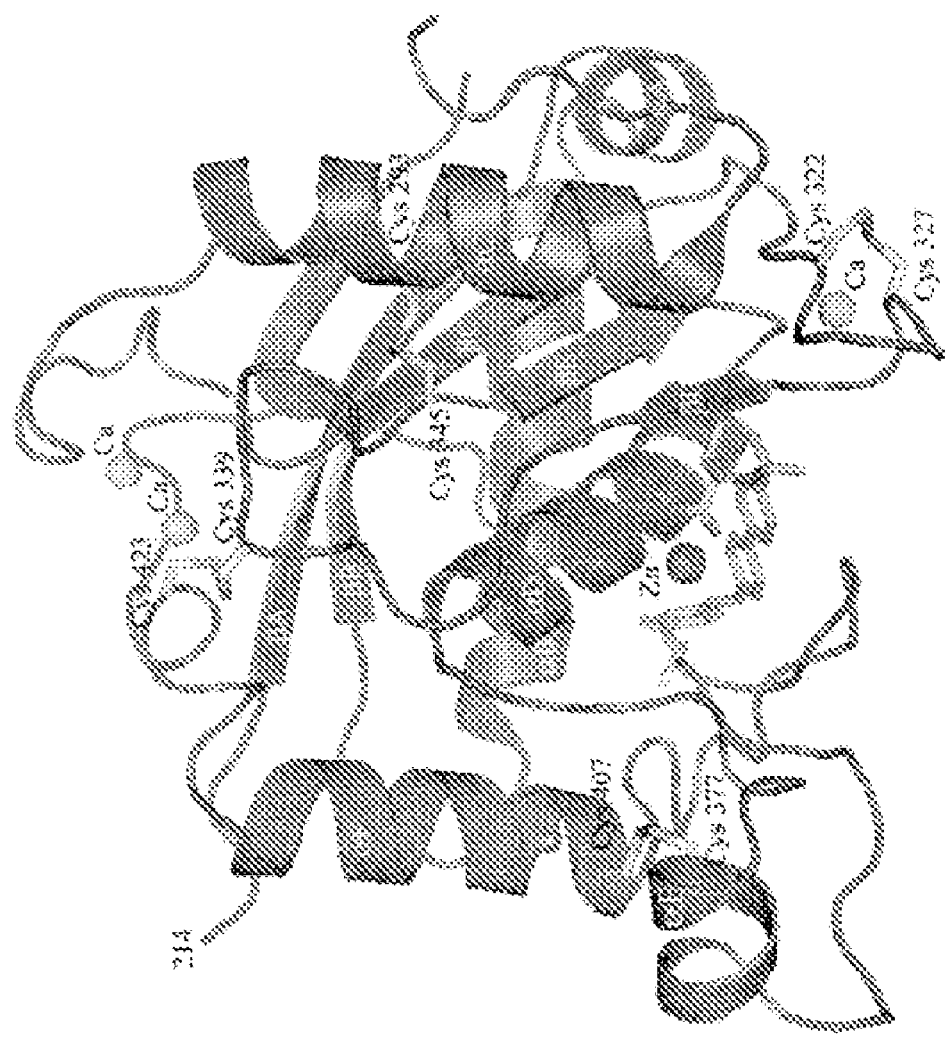
FIG. 6 is a ribbon diagram illustrating the structure of the catalytic domain of an Agg-1-A1C2/Compound 1 complex. The disulfide bonds in the Agg-1-A1C2 polypeptide are shown as sticks.

An exemplary aggrecanase polypeptide/ligand complex is a human Agg-1 polypeptide bound to the aggrecanase inhibitor (2-[4'-(4-Isobutyryl-phenoxymethyl)-biphenyl-4-sulfonylamino]-3-methyl-butyric acid) ("Compound 1"). FIG. 4 shows the structure of Compound 1, and FIG. 5 is a ribbon diagram illustrating the structure of the human Agg-1-A1C2 polypeptide bound to the inhibitor Compound 1. Structural helices are identified by "αA" through "αH", and structural sheets are indicated by "βA" through "βK." Calcium atoms and zinc atoms are also indicated. FIG. 6 is a ribbon diagram illustrating the structure of the catalytic domain of an Agg-1-A1C2/Compound 1 complex. The disulfide bonds in the Agg-1-A1C2 polypeptide are shown as sticks. The coordinates of the crystal structure of the human Agg-1 polypeptide/Compound 1 complex are provided below at Table 5.

Figure 7:
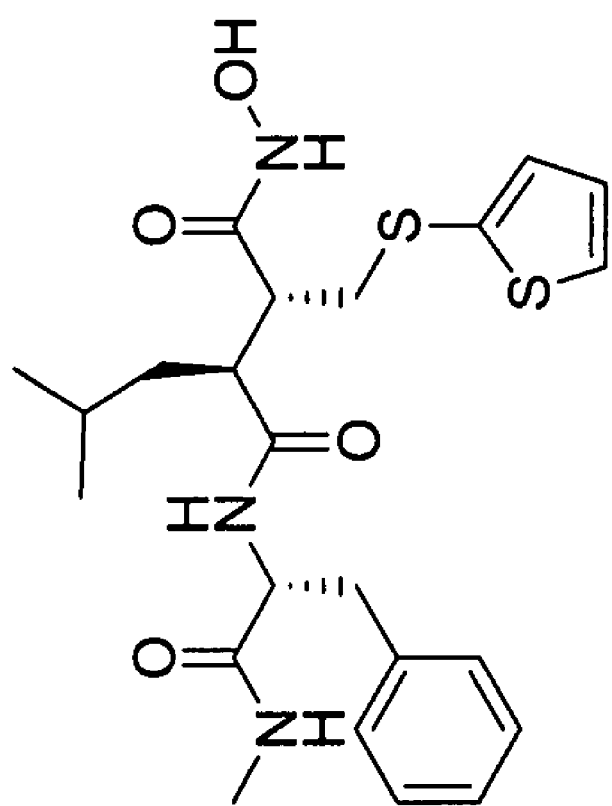
FIG. 7 is the chemical structure of batimastat.
Figure 8:
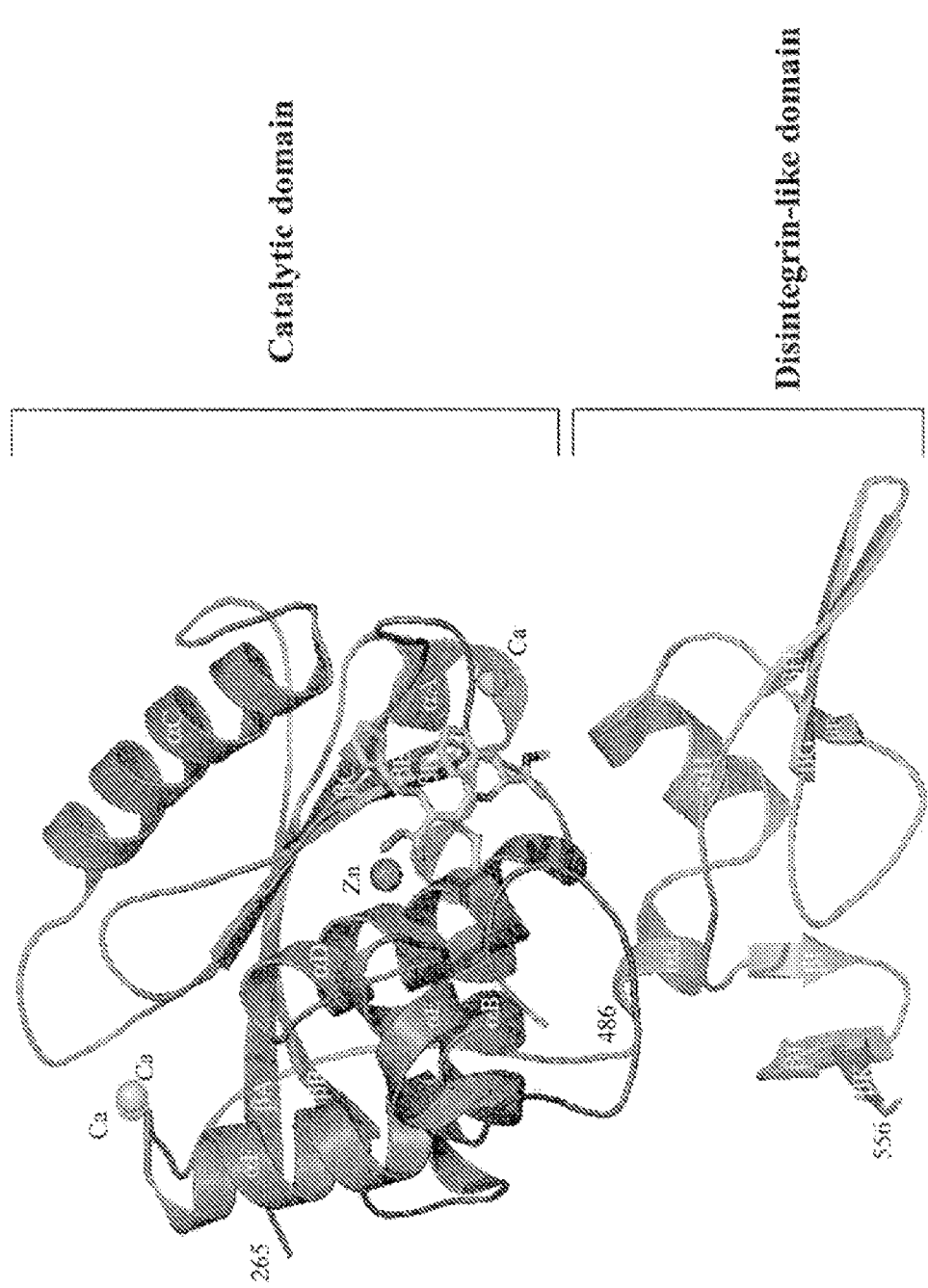
FIG. 8 is a ribbon diagram illustrating the structure of a human Agg-2 polypeptide (SEQ ID NO:3) bound to the inhibitor batimastat. Structural helices are identified by "αA," through "αH." Structural sheets are indicated by "βA" through "βK." Calcium atoms and zinc atoms are also indicated.
Figure 9:
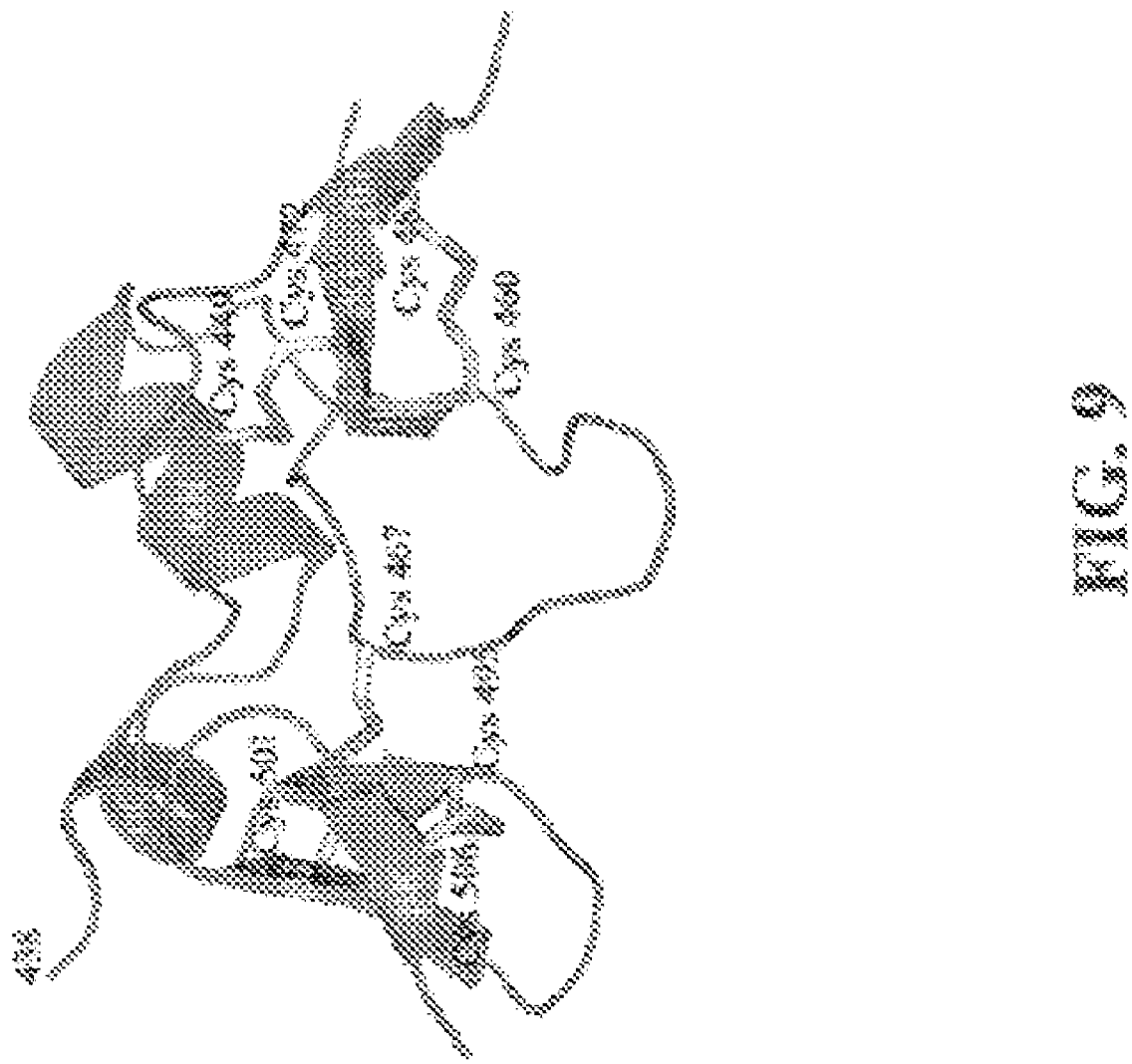
FIG. 9 is a ribbon diagram illustrating the structure of the disintegrin-like domain of an Agg-1-A1C2/Compound 1 complex. The disulfide bonds in the Agg-1-A1C2 polypeptide are shown as sticks.
Figure 10:
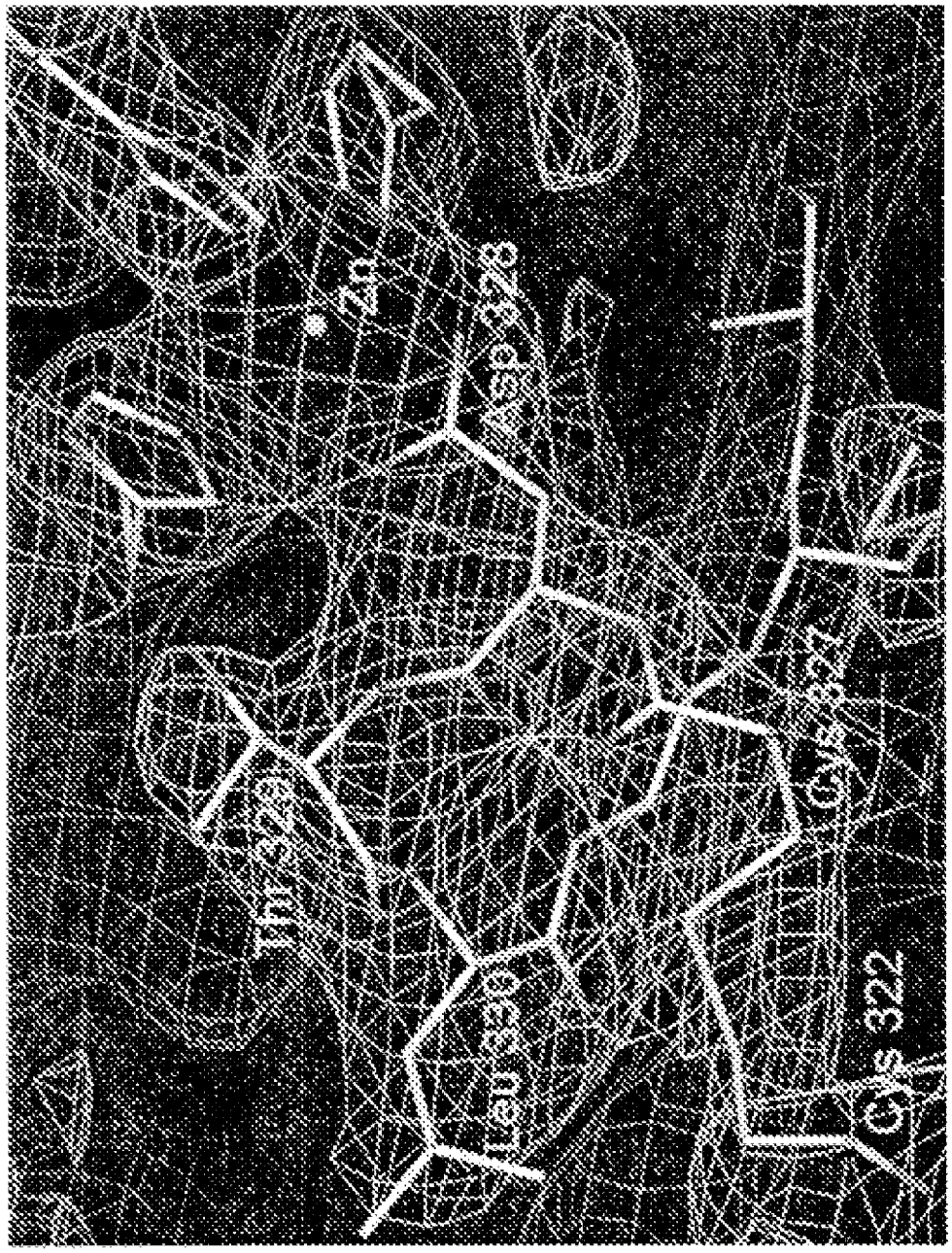
FIG. 10 is an electron density map of the active site of unliganded Agg-1-A1C2.
Figure 11:
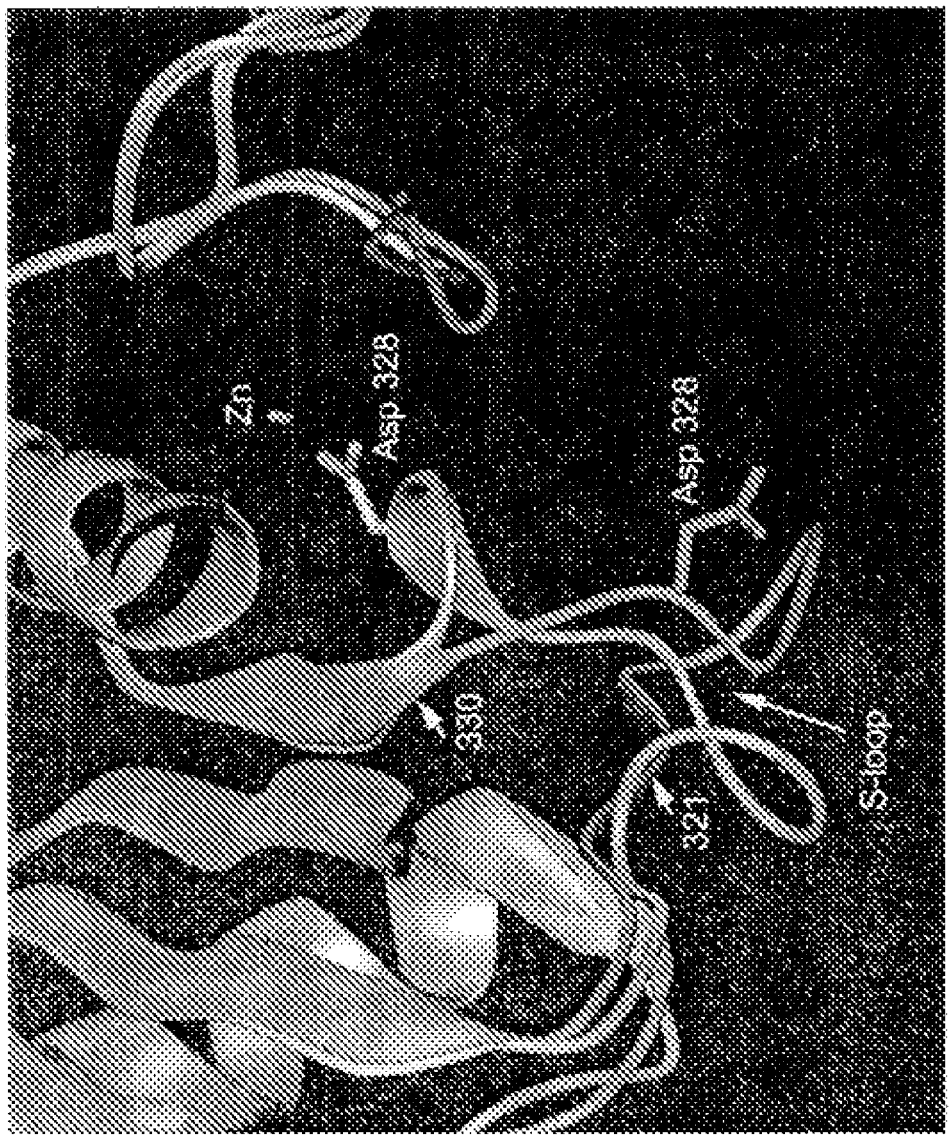
FIG. 11 is a superposition of active site structures of unliganded Agg-1-A1C2 and the Agg-1-A1C2/Compound 1 complex.

Another exemplary aggrecanase polypeptide/ligand complex is a human Agg 2 polypeptide bound to the metalloproteinase inhibitor, batimastat. FIG. 7 shows the structure of batimastat, and FIG. 8 is a ribbon diagram illustrating the structure of a human Agg-2 polypeptide (SEQ ID NO:3) bound to the inhibitor batimastat. Structural helices are identified by "αA," through "αH." Structural sheets are indicated by "βA" through "βK." Calcium atoms and zinc atoms are also indicated. FIG. 9 is a ribbon diagram illustrating the structure of the disintegrin-like domain of an Agg-1-A1C2/Compound 1 complex. The disulfide bonds in the Agg-1-A1C2 polypeptide are shown as sticks. The coordinates of the crystal structure of the human Agg-2 polypeptide/batimastat complex are provided below at Table 6.

To determine the structure of an aggrecanase, such as Agg-1 or Agg-2, a human Agg1-polypeptide or a human Agg-2 polypeptide can be prepared and crystallized as described below. In general, the human Agg-1 polypeptide or the human Agg-2 polypeptide can be prepared as desired. For example, in some embodiments, the human Agg-1 polypeptide is expressed from a DNA plasmid. The expression can be driven by a promoter, such as an inducible promoter. The human Agg-1 polypeptide can be expressed as a fusion protein with a suitable tag, such as a glutathione-S-transferase (GST), myc, HA, hexahistidine, Strep, or FLAG tag. The tag can facilitate isolation of the human Agg-1 polypeptide from cells, such as from bacterial cells or from a mammalian cell line. For example, the human Agg-1 polypeptide can be expressed in and isolated from Chinese Hamster Ovary (CHO) cells. A fusion protein can be cleaved at a protease site engineered into the fusion protein, such as at or near the site of fusion between the polypeptide and the tag. When it is desirable to form a complex between the human Agg-1 polypeptide and a ligand, such as Compound 1, the human Agg-1 polypeptide can be contacted with the ligand following cleavage and purification. For example, the human Agg-1 polypeptide can be mixed with Compound 1 prior to purification (e.g., prior to cleavage of a polypeptide tag), or the human Agg-1 polypeptide can be mixed with Compound 1 after purification. In some embodiments, Compound 1 can be mixed with the human Agg-1 polypeptide prior to purification and again following purification.

The described methods can also be used for the expression and purification of the human Agg-2 polypeptide. A ligand such as batimastat can be mixed with the human Agg-2 polypeptide prior to purification, after purification, or both prior to and following purification.

The human Agg-1 polypeptide or the human Agg-2 polypeptide can be placed in solution for collecting spectral data, NMR data, or for growing a crystal. For example, the human Agg-1 polypeptide or the human Agg-2 polypeptide can be crystallized in the presence of a salt (e.g., a sodium salt), a polymer (e.g., polyethylene glycol (PEG)), and/or an organic solvent. Crystals can be grown by various methods, such as, for example, sitting or hanging drop vapor diffusion. In general, crystallization can be performed at a temperature of from about 4° C. to about 60° C. (e.g., from about 4° C. to about 45° C., such as at about 4° C., about 15° C., about 18° C., about 20° C., about 25° C., about 30° C., about 32° C., about 35° C., about 37° C.).

In certain embodiments, the human Agg-1 polypeptide and Compound 1, or the human Agg-2 polypeptide and batimastat, can be combined in a solution for collecting spectral data for the human Agg-1 polypeptide/Compound 1 complex or the human Agg-2 polypeptide/batimastat complex, for collecting NMR data for either of these two complexes, or for growing a crystal of either of these two complexes as described above.

In general, a crystal of the human Agg-1 polypeptide or the human Agg-2 polypeptide can diffract X-rays to a resolution of about 3.5 Å or less (e.g., about 3.2 Å or less, about 3.0 Å or less, about 2.5 Å or less, about 2.4 Å or less, about 2.3 Å or less, about 2.2 Å or less, about 2.1 Å or less, about 2.0 Å or less, about 1.9 Å or less, about 1.8 Å or less, about 1.7 Å or less, about 1.6 Å or less, about 1.5 Å or less, or about 1.4 Å or less). In some embodiments, a crystal of the human Agg-1 polypeptide or the human Agg-2 polypeptide can diffract X-rays to a resolution of from about 1.7 Å to about 3.0 Å (e.g., the crystal of the human Agg-1 polypeptide can diffract X-rays to about 2.0 to about 2.8 Å).

In general, a crystal of the human Agg-1 polypeptide bound to Compound 1 or the human Agg-2 polypeptide bound to batimastat can diffract X-rays to a resolution of about 3.5 Å or less (e.g., about 3.2 Å or less, about 3.0 Å or less, about 2.5 Å or less, about 2.4 Å or less, about 2.3 Å or less, about 2.2 Å or less, about 2.1 Å or less, about 2.0 Å or less, about 1.9 Å or less, about 1.8 Å or less, about 1.7 Å or less, about 1.6 Å or less, about 1.5 Å or less, or about 1.4 Å or less). In some embodiments, a crystal of the human Agg-1 polypeptide bound to Compound 1 or the human Agg-2 polypeptide bound to batimastat can diffract X-rays to a resolution of from about 1.7 Å to about 3.0 Å (e.g., the crystal of the human Agg-1 polypeptide bound to Compound 1 can diffract X-rays to about 2.8 Å, and the crystal of the human Agg-2 polypeptide bound to batimastat can diffract X-rays to about 2.9 Å).

In certain embodiments, a crystal of the human Agg-1 polypeptide belongs to space group $P2_1$ with unit cell parameters a=128.28 Å, b=83.63 Å, c=150.16 Å, $\beta$=112.409°. In other embodiments, a crystal of the human Agg-1 polypeptide bound to Compound 1 belongs to space group $P2_1$ with unit cell parameters a=82.07 Å, b=83.96 Å, c=98.95 Å, $\beta$=89.9°. In other embodiments, a crystal of the human Agg-2 polypeptide bound to batimastat belongs to space group $P3_1$ with unit cell parameters a=93.64 Å, b=93.64 Å, c=92.59 Å, $\gamma$=120°. The space group refers to the overall symmetry of the crystal, and includes point symmetry and space symmetry. In certain embodiments, a crystal of the human Agg-1 polypeptide can contain eight molecules of the human Agg-1 polypeptide in the asymmetric unit, a crystal of the human Agg-1 polypeptide bound to Compound 1 can contain four molecules of the complex in the asymmetric unit, or a crystal of the human Agg-2 polypeptide bound to batimastat can contain two molecules of the complex in the asymmetric unit. The asymmetric unit is the smallest unit from which the crystal structure can be generated by making use of the symmetry operations of the space group. A crystal is generally made up of the motif defined by the space-group symmetry operations on the asymmetric units, and a translation of that motif through the crystal lattice.

Structural data describing a crystal can be obtained, for example, by X-ray diffraction. X-ray diffraction data can be collected by a variety of sources, X-ray wavelengths and detectors. In some embodiments, rotating anodes and synchrotron sources (e.g., Advanced Light Source (ALS), Berkeley, Calif.; or Advanced Photon Source (APS), Argonne, Ill.) can be used as the source(s) of X-rays. In certain embodiments, X-rays for generating diffraction data can have a wavelength of from about 0.5 Å to about 1.6 Å (e.g., about 0.7 Å, about 0.9 Å, about 1.0 Å, about 1.1 Å, about 1.3 Å, about 1.4 Å, about 1.5 Å, or about 1.6 Å). In some embodiments, area detectors and/or charge-couple devices (CCDs) can be used as the detector(s).

X-ray diffraction data of a crystal of the human Agg-1 polypeptide or the human Agg-2 polypeptide, or a complex of the human Agg-1 polypeptide bound to Compound 1 or the human Agg-2 polypeptide bound to batimastat can be used to obtain the structural coordinates of the atoms in the complex. The structural coordinates are Cartesian coordinates that describe the location of atoms in three-dimensional space in relation to other atoms in the complex. For example, the structural coordinates listed in Table 4 are the structural coordinates of a crystalline human Agg-1 polypeptide. The structural coordinates listed in Tables 5 and 6 are the structural coordinates of a crystalline complex of the human Agg-1 polypeptide bound to Compound 1 and the human Agg-2 polypeptide bound to batimastat, respectively. The structural coordinates of Table 4 describe the location of atoms of the human Agg-1 polypeptide in relation to each other and the structural coordinates of Table 5 describe the location of atoms of the human Agg-1 polypeptide in relation to each other when the human Agg-1 polypeptide is bound to Compound 1. The structural coordinates of Table 5 also describe the location of atoms in the human Agg-1 polypeptide in relation to the atoms in Compound 1, and the location of atoms in Compound 1 in relation to each other. The structural coordinates of Table 6 describe the location of atoms of the human Agg-2 polypeptide in relation to each other when the human Agg-2 polypeptide is bound to batimastat, the location of atoms in the human Agg-2 polypeptide in relation to the atoms in batimastat, and the location of atoms in batimastat in relation to each other. The structural coordinates can be modified by mathematical manipulation, such as by inversion or integer additions or subtractions. As such, structural coordinates are relative coordinates. For example, structural coordinates describing the location of atoms in the human Agg-1 polypeptide, or the human Agg-1 polypeptide bound to Compound 1, or the human Agg-2 polypeptide bound to batimastat are not specifically limited by the actual x, y, and z coordinates of Tables 4, 5, and 6, respectively.

The structural coordinates of the human Agg-1 polypeptide can be used to derive a representation of the polypeptide or a fragment of the polypeptide. In addition, the structural coordinates of a complex of the human Agg-1 polypeptide bound to Compound 1 or the human Agg-2 polypeptide bound to batimastat can be used to derive a representation (e.g., a two dimensional representation or three dimensional representation) of the complex, a fragment of the complex, the human Agg-1 polypeptide or the human Agg-2 polypeptide, or a fragment of the human Agg-1 polypeptide or the human Agg-2 polypeptide. Such representations can be useful for a number of applications, including, for example, the visualization, identification and characterization of an active site of the polypeptide. In certain embodiments, a three-dimensional representation can include the structural coordinates of the human Agg-1 polypeptide according to Tables 4 or 5, ±a root mean square (rms) deviation from the alpha carbon atoms of amino acids of not more than about 1.5 Å (e.g., not more than about 1.0 Å, not more than about 0.5 Å). In certain other embodiments, a three-dimensional representation can include the structural coordinates of the human Agg-2 polypeptide according to Table 6.

RMS deviation is the square root of the arithmetic mean of the squares of the deviations from the mean, and is a way of expressing deviation or variation from structural coordinates. Conservative substitutions (see discussion below) of amino acids can result in a molecular representation having structural coordinates within the stated rms deviation. For example, two molecular models of polypeptides that differ from one another by conservative amino acid substitutions can have coordinates of backbone atoms within a stated rms deviation, such as less than about 1.5 Å (e.g., less than about 1.0 Å, less than about 0.5 Å). Backbone atoms of a polypeptide include the alpha carbon ($C_\alpha$ or CA) atoms, carbonyl carbon (C) atoms, and amide nitrogen (N) atoms.

Various software programs allow for the graphical representation of a set of structural coordinates to obtain a representation of the human Agg-1 polypeptide, a complex of the human Agg-1 polypeptide bound to Compound 1 or the human Agg-2 polypeptide bound to batimastat, or a fragment of one of these complexes. In general, such a representation should accurately reflect (relatively and/or absolutely) structural coordinates, or information derived from structural coordinates, such as distances or angles between features. In some embodiments, the representation is a two-dimensional figure, such as a stereoscopic two-dimensional figure. In certain embodiments, the representation is an interactive two-dimensional display, such as an interactive stereoscopic two-dimensional display. An interactive two-dimensional display can be, for example, a computer display that can be rotated to show different faces of a polypeptide, a fragment of a polypeptide, a complex and/or a fragment of a complex. In some embodiments, the representation is a three-dimensional representation. As an example, a three-dimensional model can be a physical model of a molecular structure (e.g., a ball-and-stick model). As another example, a three dimensional representation can be a graphical representation of a molecular structure (e.g., a drawing or a figure presented on a computer display). A two-dimensional graphical representation (e.g., a drawing) can correspond to a three-dimensional representation when the two-dimensional representation reflects three-dimensional information, for example, through the use of perspective, shading, or the obstruction of features more distant from the viewer by features closer to the viewer. In some embodiments, a representation can be modeled at more than one level. As an example, when the three-dimensional representation includes a polypeptide, such as a human Agg-1 polypeptide or a human Agg-2 polypeptide, or a complex, such as a complex of the human Agg-1 polypeptide bound to Compound 1 or the human Agg-2 polypeptide bound to batimastat, the polypeptide can be represented at one or more different levels of structure, such as primary (amino acid sequence), secondary (e.g., α-helices and β-sheets), tertiary (overall fold), and quaternary (oligomerization state) structure. A representation can include different levels of detail. For example, the representation can include the relative locations of secondary structural features of a protein without specifying the positions of atoms. A more detailed representation could, for example, include the positions of atoms.

In some embodiments, a representation can include information in addition to the structural coordinates of the atoms in the human Agg-1 polypeptide, a complex of the human Agg-1 polypeptide bound to Compound 1 or the human Agg-2 polypeptide bound to batimastat. For example, a representation can provide information regarding the shape of a solvent accessible surface, the van der Waals radii of the atoms of the model, and the van der Waals radius of a solvent (e.g., water). Other features that can be derived from a representation include, for example, electrostatic potential, the location of voids or pockets within a macromolecular structure, and the location of hydrogen bonds and salt bridges.

An agent that interacts with (e.g., binds) the human Agg-1 polypeptide or the human Agg-2 polypeptide can be identified or designed by a method that includes using a representation of either polypeptide or a fragment of either polypeptide, or a complex of the human Agg-1 polypeptide bound to Compound 1 or the human Agg-2 polypeptide bound to batimastat, or a fragment of either of these complexes. Exemplary types of representations include the representations discussed above. In some embodiments, the representation can be of an analog polypeptide, polypeptide fragment, complex or fragment of a complex. A candidate agent that interacts with the representation can be designed or identified by performing computer fitting analysis of the candidate agent with the representation. In general, an agent is a molecule. Examples of agents include polypeptides, nucleic acids (including DNA or RNA), steroids and non-steroidal organic compounds. An agent that interacts with a polypeptide (e.g., a human Agg-1 polypeptide or a human Agg-2 polypeptide) can interact transiently or stably with the polypeptide. The interaction can be mediated by any of the forces noted herein, including, for example, hydrogen bonding, electrostatic forces, hydrophobic interactions, and van der Waals interactions.

As noted above, X-ray crystallography can be used to obtain structural coordinates of a complex of the human Agg-1 polypeptide bound to Compound 1 or the human Agg-2 polypeptide bound to batismatat. However, such structural coordinates can be obtained using other techniques including NMR techniques. Additional structural information can be obtained from spectral techniques (e.g., optical rotary dispersion (ORD), circular dichroism (CD)), homology modeling, and computational methods (e.g., computational methods that can include data from molecular mechanics, computational methods that include data from dynamics assays).

In some embodiments, the X-ray diffraction data can be used to construct an electron density map of the human Agg-1 polypeptide, a complex of the human Agg-1 polypeptide bound to Compound 1 or the human Agg-2 polypeptide bound to batimastat, or a fragment of the polypeptide or a fragment of the complex, and the electron density map can be used to derive a representation (e.g., a two dimensional representation, a three dimensional representation) of the human Agg-1 polypeptide, the human Agg-1 polypeptide bound to Compound 1, or the human Agg-2 polypeptide bound to batimastat, or a fragment of the polypeptide or of either complex. Creation of an electron density map typically involves using information regarding the phase of the X-ray scatter. Phase information can be extracted, for example, either from the diffraction data or from supplementing diffraction experiments to complete the construction of the electron density map. Methods for calculating phase from X-ray diffraction data include, for example, multiwavelength anomalous dispersion (MAD), multiple isomorphous replacement (MIR), multiple isomorphous replacement with anomalous scattering (MIRAS), single isomorphous replacement with anomalous scattering (SIRAS), reciprocal space solvent flattening, molecular replacement, or any combination thereof. These methods generate phase information by making isomorphous structural modifications to the native protein, such as by including a heavy atom or changing the scattering strength of a heavy atom already present, and then measuring the diffraction amplitudes for the native protein and each of the modified cases. If the position of the additional heavy atom or the change in its scattering strength is known, then the phase of each diffracted X-ray can be determined by solving a set of simultaneous phase equations. The location of heavy atom sites can be identified using a computer program, such as SHELXS (Sheldrick, Institut Anorg. Chemie, Göttingen, Germany), and diffraction data can be processed using computer programs such as MOSFLM, SCALA, SOLOMON, and SHARP ("The CCP4 Suite: Programs for Protein Crystallography," *Acta Crystallogr*. Sect. D, 54:905-921, 1997; deLa Fortelle and Brigogne, *Meth. Enzym.* 276:472-494, 1997). The phase of X-ray scatter for a crystalline human Agg-1 polypeptide bound to Compound 1, for example, can be determined by MAD using crystals of a selenomethionine substituted protein. To create a selenomethionine substituted protein, mammalian cells expressing the human Agg-1 nucleic acid can be cultured in the presence of selenomethionine. The selenomethionine-substituted protein is purified, contacted with Compound 1, and the complex crystallized by a standard method, such as by the hanging drop technique. Phases obtained by MAD from crystals of the native and selenomethionine substituted protein each complexed with Compound 1 can then be used to create an electron density map of the complex.

The electron density map can be used to derive a representation of a polypeptide, a complex, or a fragment of a polypeptide or complex by aligning a three-dimensional model of a polypeptide or complex (e.g., a complex containing a polypeptide bound to a ligand) with the electron density map. For example, the electron density map corresponding to the human Agg-1 polypeptide can be aligned with the electron density map corresponding to the human Agg-1 polypeptide/Compound 1 complex derived by an isomorphous replacement method. The human Agg-2 polypeptide/batimastat complex can be aligned with the electron density map corresponding to the human Agg-1 polypeptide complexed to Compound 1.

The alignment process results in a comparative model that shows the degree to which the calculated electron density map varies from the model of the previously known polypeptide or the previously known complex. The comparative model is then refined over one or more cycles (e.g., two cycles, three cycles, four cycles, five cycles, six cycles, seven cycles, eight cycles, nine cycles, ten cycles) to generate a better fit with the electron density map. A software program such as CNS (Brunger et al., *Acta Crystallogr*. D54:905-921, 1998) can be used to refine the model. The quality of fit in the comparative model can be measured by, for example, an $R_{work}$ or $R_{free}$ value. A smaller value of $R_{work}$ or $R_{free}$ generally indicates a better fit. Misalignments in the comparative model can be adjusted to provide a modified comparative model and a lower $R_{work}$ or $R_{free}$ value. The adjustments can be based on information (e.g., sequence information) relating to the human Agg-1 polypeptide, the human Agg-2 polypeptide, Compound 1, batimastat, the human Agg-1 polypeptide/Compound 1 complex or the human Agg-2 polypeptide/batimastat complex, as appropriate. As an example, in embodiments in which a model of a previously known complex of a polypeptide bound to a ligand is used, such as the human Agg-1 polypeptide bound to Compound 1, an adjustment can include replacing the Compound 1 of the complex with a different ligand, such as batimastat. As another example, in certain embodiments, an adjustment can include replacing an amino acid in the previously known polypeptide (e.g., the human Agg-1 polypeptide) with the amino acid in the corresponding site of a different aggrecanase, such as the human Agg-2 polypeptide. When adjustments to the modified comparative model satisfy a best fit to the electron density map, the resulting model is that which is determined to describe the polypeptide or complex from which the X-ray data was derived. Methods of such processes are disclosed, for example, in Carter and Sweet, eds., "Macromolecular Crystallography" in *Methods in Enzymology*, Vol. 277, Part B, New York: Academic Press, 1997, and articles therein, e.g., Jones and Kjeldgaard, "Electron-Density Map Interpretation," p. 173, and Kleywegt and Jones, "Model Building and Refinement Practice," p. 208.

Discussed above is a method of deriving a representation of a complex by aligning a three-dimensional model of a previously known polypeptide or a previously known complex with a newly calculated electron density map corresponding to a crystal of the polypeptide or the complex. One adjustment that can be used in this modeling process can include replacing the compound in the representation of the previously known complex with Compound 1 or batimastat.

A machine, such as a computer, can be programmed in memory with the structural coordinates of the human Agg-1 polypeptide, or a complex of the human Agg-1 polypeptide bound to Compound 1 or the human Agg-2 polypeptide bound to batimastat, together with a program capable of generating a graphical representation of the structural coordinates on a display connected to the machine. Alternatively or additionally, a software system can be designed and/or utilized to accept and store the structural coordinates. The software system can be capable of generating a graphical representation of the structural coordinates. The software system can also be capable of accessing external databases to identify compounds with similar structural features as Compound 1 or batimastat, and/or to identify one or more candidate agents with characteristics that may render the candidate agent(s) likely to interact with the human Agg-1 polypeptide or the human Agg-2 polypeptide.

A machine having a memory containing structure data or a software system containing such data can aid in the rational design or selection of a human Agg-1 polypeptide agonist, a human Agg-1 polypeptide antagonist, a human Agg-2 polypeptide agonist, or a human Agg-2 polypeptide antagonist. For example, such a machine or software system can aid in the evaluation of the ability of an agent to associate with a complex of the human Agg-1 polypeptide bound to Compound 1 or the human Agg-2 polypeptide bound to batimastat, or can aid in the modeling of compounds or proteins related by structural or sequence homology to the human Agg-1 polypeptide or the human Agg-2 polypeptide. As used herein, an agonist refers to a compound that enhances at least one activity of the human Agg-1 polypeptide or the human Agg-2 polypeptide. An antagonist refers to a compound that inhibits or counteracts at least one activity of the human Agg-1 polypeptide or the human Agg-2 polypeptide. For example, a compound, such as Compound 1 or batimastat may function as an antagonist of the human Agg-1 polypeptide or the human Agg-2 polypeptide by, for example, decreasing the rate of aggrecan cleavage by the human Agg-1 polypeptide or the human Agg-2 polypeptide, or by inhibiting interaction of the human Agg-1 polypeptide or the human Agg-2 polypeptide with aggrecan, thereby inhibiting aggrecan cleavage.

The machine can produce a representation (e.g., a two dimensional representation, a three dimensional representation) of a complex of the human Agg-1 polypeptide bound to Compound 1 or the human Agg-2 polypeptide bound to batimastat or a fragment of either complex. A software system, for example, can cause the machine to produce such information. The machine can include a machine-readable data storage medium including a data storage material encoded with machine-readable data. The machine-readable data can include structural coordinates of atoms of a complex of the human Agg-1 polypeptide bound to Compound 1 or the human Agg-2 polypeptide bound to batimastat or a fragment of either complex. Machine-readable storage media (e.g., data storage material) include, for example, conventional computer hard drives, floppy disks, DAT tape, CD-ROM, DVD, and other magnetic, magneto-optical, optical, and other media which may be adapted for use with a machine (e.g., a computer). The machine can also have a working memory for storing instructions for processing the machine-readable data, as well as a central processing unit (CPU) coupled to the working memory and to the machine-readable data storage medium for the purpose of processing the machine-readable data into the desired three-dimensional representation. A display can be connected to the CPU so that the three-dimensional representation can be visualized by the user. Accordingly, when used with a machine programmed with instructions for using the data (e.g., a computer loaded with one or more programs of the sort described herein) the machine is capable of displaying a graphical representation (e.g., a two dimensional graphical representation, a three-dimensional graphical representation) of any of the polypeptides, polypeptide fragments, complexes, or complex fragments described herein.

A display (e.g., a computer display) can show a representation of the human Agg-1 polypeptide or the human Agg-2 polypeptide, or a complex of the human Agg-1 polypeptide bound to Compound 1 or a complex of the human Agg-2 polypeptide bound to batimastat, or a fragment the human Agg-1 polypeptide or the human Agg-2 polypeptide or a fragment of either complex. The user can inspect the representation and, using information gained from the representation, generate a model of the human Agg-1 polypeptide or polypeptide fragment bound to a ligand, or a complex or fragment thereof that includes an agent other than Compound 1 or batimastat. The model can be generated, for example, by altering a previously existing representation of the human Agg-1 polypeptide, the human Agg-1 polypeptide/Compound 1 complex or the human Agg-2 polypeptide/batimastat complex. Optionally, the user can superimpose a three-dimensional model of an agent on the representation of the human Agg-1 polypeptide, or the human Agg-1 polypeptide bound to Compound 1 or the human Agg-2 polypeptide bound to batimastat. The agent can be an agonist (e.g., a candidate agonist) of the human Agg-1 polypeptide or the human Agg-2 polypeptide, or an antagonist (e.g., a candidate antagonist) of the human Agg-1 polypeptide or the human Agg-2 polypeptide. In some embodiments, the agent can be a known compound or a fragment of a known compound. In certain embodiments, the agent can be a previously unknown compound, or a fragment of a previously unknown compound.

It can be desirable for the agent to have a shape that complements the shape of the active site. There can be a preferred distance, or range of distances, between atoms of the agent and atoms of the human Agg-1 polypeptide or the human Agg-2 polypeptide. Distances longer than a preferred distance may be associated with a weak interaction between the agent and active site (e.g., the active site of the human Agg-1 polypeptide or the human Agg-2 polypeptide). Distances shorter than a preferred distance may be associated with repulsive forces that can weaken the interaction between the agent and the polypeptide. A steric clash can occur when distances between atoms are too short. A steric clash occurs when the locations of two atoms are unreasonably close together, for example, when two atoms are separated by a distance less than the sum of their van der Waals radii. If a steric clash exists, the user can adjust the position of the agent relative to the human Agg-1 polypeptide or the human Agg-2 polypeptide (e.g., a rigid body translation or rotation of the agent) until the steric clash is relieved. The user can adjust the conformation of the agent or of the human Agg-1 polypeptide or the human Agg-2 polypeptide in the vicinity of the agent in order to relieve a steric clash. Steric clashes can also be removed by altering the structure of the agent, for example, by changing a "bulky group," such as an aromatic ring, to a smaller group, such as to a methyl or hydroxyl group, or by changing a rigid group to a flexible group that can accommodate a conformation that does not produce a steric clash. Electrostatic forces can also influence an interaction between an agent and a ligand-binding domain. For example, electrostatic properties can be associated with repulsive forces that can weaken the interaction between the agent and the human Agg-1 polypeptide or the human Agg-2 polypeptide. Electrostatic repulsion can be relieved by altering the charge of the agent, e.g., by replacing a positively charged group with a neutral group.

Forces that influence binding strength between Compound 1 or batimastat and the human Agg-1 polypeptide or the human Agg-2 polypeptide, respectively, can be evaluated in the polypeptide/agent model. These can include, for example, hydrogen bonding, electrostatic forces, hydrophobic interactions, van der Waals interactions, dipole-dipole interactions, π-stacking forces, and cation-π interactions. The user can evaluate these forces visually, for example by noting a hydrogen bond donor/acceptor pair arranged with a distance and angle suitable for a hydrogen bond. Based on the evaluation, the user can alter the model to find a more favorable interaction between the human Agg-1 polypeptide or the human Agg-2 polypeptide and the agent. Altering the model can include changing the three-dimensional structure of the polypeptide without altering its chemical structure, for example by altering the conformation of amino acid side chains or backbone dihedral angles. Altering the model can include altering the position or conformation of the agent, as described above. Altering the model can also include altering the chemical structure of the agent, for example by substituting, adding, or removing groups. For example, if a hydrogen bond donor on the human Agg-1 polypeptide or the human Agg-2 polypeptide is located near a hydrogen bond donor on the agent, the user can replace the hydrogen bond donor on the agent with a hydrogen bond acceptor.

The relative locations of an agent and the human Agg-1 polypeptide or the human Agg-2 polypeptide, or their conformations, can be adjusted to find an optimized binding geometry for a particular agent to the human Agg-1 polypeptide or the human Agg-2 polypeptide. An optimized binding geometry is characterized by, for example, favorable hydrogen bond distances and angles, maximal electrostatic attractions, minimal electrostatic repulsions, the sequestration of hydrophobic moieties away from an aqueous environment, and the absence of steric clashes. The optimized geometry can have the lowest calculated energy of a family of possible geometries for the human Agg-1 polypeptide/agent complex or the human Agg-2 polypeptide/agent complex. An optimized geometry can be determined, for example, through molecular mechanics or molecular dynamics calculations.

A series of representations of the human Agg-1 polypeptide, or complexes of the human Agg-1 polypeptide bound to Compound 1, or complexes of the human Agg-2 polypeptide bound to batimastat, having different bound agents can be generated. A score can be calculated for each representation. The score can describe, for example, an expected strength of interaction between the human Agg-1 polypeptide or the human Agg-2 polypeptide and the agent. The score can reflect one of the factors described above that influence binding strength. The score can be an aggregate score that reflects more than one of the factors. The different agents can be ranked according to their scores.

Steps in the design of the agent can be carried out in an automated fashion by a machine. For example, a representation of the human Agg-1 polypeptide or the human Agg-2 polypeptide can be programmed in the machine, along with representations of candidate agents. The machine can find an optimized binding geometry for each of the candidate agents to the active site, and calculate a score to determine which of the agents in the series is likely to interact most strongly with the human Agg-1 polypeptide or the human Agg-2 polypeptide.

A software system can be designed and/or implemented to facilitate these steps. Software systems (e.g., computer programs) used to generate representations or perform the fitting analyses include, for example: MCSS, Ludi, QUANTA, Insight II, Cerius2, CHARMm, and Modeler from Accelrys, Inc. (San Diego, Calif.); SYBYL, Unity, FleXX, and LEAPFROG from TRIPOS, Inc. (St. Louis, Mo.); AUTODOCK (Scripps Research Institute, La Jolla, Calif.); GRID (Oxford University, Oxford, UK); DOCK (University of California, San Francisco, Calif.); and Flo+ and Flo99 (Thistlesoft, Morris Township, N.J.). Other useful programs include ROCS, ZAP, FRED, Vida, and Szybki from Openeye Scientific Software (Santa Fe, N. Mex.); Maestro, Macromodel, and Glide from Schrodinger, LLC (Portland, Oreg.); MOE (Chemical Computing Group, Montreal, Quebec), Allegrow (Boston De Novo, Boston, Mass.), CNS (Brunger, et al., *Acta Crystall.* Sect. D 54:905-921, 1997) and GOLD (Jones et al., *J. Mol. Biol.* 245:43-53, 1995). The structural coordinates can also be used to visualize the three-dimensional structure of the human Agg-1 polypeptide, or a complex of the human Agg-1 polypeptide bound to Compound 1 or the human Agg-2 polypeptide bound to batimastat using MOLSCRIPT, RASTER3D, or PYMOL (Kraulis, *J. Appl. Crystallogr.* 24: 946-950, 1991; Bacon and Anderson, *J. Mol. Graph.* 6: 219-220, 1998; DeLano, The PYMOL Molecular Graphics System (2002) DeLano Scientific, San Carlos, Calif.).

The agent can, for example, be selected by screening an appropriate database, can be designed de novo by analyzing the steric configurations and charge potentials of a human Agg-1 polypeptide or a human Agg-2 polypeptide in conjunction with the appropriate software systems, and/or can be designed using characteristics of known ligands of other aggrecanase enzymes or other metalloproteinases. The method can be used to design or select agonists or antagonists of the human Agg-1 polypeptide or the human Agg-2 polypeptide. A software system can be designed and/or implemented to facilitate database searching, and/or agent selection and design.

Once an agent has been designed or identified, it can be obtained or synthesized and further evaluated for its effect on the human Agg-1 polypeptide or the human Agg-2 polypeptide activity. For example, the agent can be evaluated by contacting it with the human Agg-1 polypeptide or the human Agg-2 polypeptide and measuring the effect of the agent on polypeptide activity. A method for evaluating the agent can include an activity assay performed in vitro or in vivo. For example, an activity assay performed in vitro can be a fluorescence-based assay. Agents can be assessed by their ability to inhibit cleavage of a fluorescent peptide substrate, such as Abz-TEGARGSVI-Dap(Dnp) (SEQ ID NO: 35) (Abz:o-aminobenzoyl; Dnp: 2,4 dinitrophenyl) (Anaspec, Inc., San Jose, Calif.). The peptide sequence TEGARGSVI (SEQ ID NO: 15) is based on the amino acid sequence of the Glu373-Ala374 cleavage site of aggrecan in osteoarthritis. Candidate compounds can be pre-incubated with a purified human Agg-1 polypeptide for 10 min. and then the peptide substrate can be added to the combination at temperatures ranging from 25° C. to 37° C., typically at 30° C. Cleavage of the Glu-Ala bond releases the fluorophore from internal quenching. This results in an increase in fluorescence monitored at $\lambda_{ex}$ 340 nm and $\lambda_{ex}$ 420 nm over a period of 40 min. The initial rate (v) at each concentration of the substrate is fit to the following equation:

$$V=V_{max}-S^h/(S_{0.5})^h+S^h)$$

where h is the Hill constant and $S_{0.5}$ is the substrate concentration at half the $V_{max}$. The percentage activity remaining in the presence of inhibitor is plotted as a function of inhibitor concentration, and the $IC_{50}$ value is determined by fitting the data to the following equation:

$$\%\ activity=100IC_{50}/(I^o+IC_{50})$$

where $I_o$ is initial concentration of inhibitor.

An activity assay can be an in vivo assay, such as a cell-based assay. A cell based assay can include monitoring the effect of a candidate agent on aggrecan cleavage. Such assays for the inhibitors may involve contacting the inhibitor with cells expressing the human Agg-1 polypeptide and aggrecan, and then measuring aggrecan cleavage, such as by detecting and measuring aggrecan fragments produced by cleavage at the aggrecanase susceptible site. Aggrecan fragments can be detected by standard protein detection techniques, such as immunohistochemical analysis methods.

Depending upon the action of the agent on the human Agg-1 polypeptide or the human Agg-2 polypeptide, the agent can act either as an agonist or antagonist of the human Agg-1 polypeptide activity or the human Agg-2 polypeptide activity. An agonist, for example, may increase the rate of aggrecan cleavage or increase the binding affinity of the human Agg-1 polypeptide or the human Agg-2 polypeptide to aggrecan. Conversely, an antagonist may decrease the rate of aggrecan cleavage or decrease the binding affinity of the human Agg-1 polypeptide or the human Agg-2 polypeptide to aggrecan. The agent can be contacted with the human Agg-1 polypeptide or the human Agg-2 polypeptide in the presence of an aggrecan substrate in order to determine whether or not the agent inhibits binding of the human Agg-1 polypeptide or the human Agg-2 polypeptide to the aggrecan substrate. A crystal containing the human Agg-1 polypeptide or the human Agg-2 polypeptide bound to the identified agent can be grown and the structure determined by X-ray crystallography. A second agent can be designed or identified based on the interaction of the first agent with the human Agg-1 polypeptide or the human Agg-2 polypeptide.

Various molecular analysis and rational drug design techniques are further disclosed in, for example, U.S. Pat. Nos. 5,834,228, 5,939,528 and 5,856,116, as well as in PCT Application No. PCT/US98/16879, published as WO 99/09148.

While certain embodiments have been described, other embodiments are also contemplated.

As an example, while embodiments involving the human Agg-1 polypeptide, the human Agg-1 polypeptide bound to Compound 1, and the human Agg-2 polypeptide bound to batimastat have been described, the description herein is more generally directed to any aggrecanase polypeptide and any ligand.

An aggrecanase polypeptide can be a full-length, mature polypeptide, including the full-length amino acid sequence of any isoform of an aggrecanase polypeptide. An isoform is any of several multiple forms of a protein that differ in their primary structure.

An aggrecanase polypeptide can be a fragment of a human Agg-1 polypeptide or a fragment of a human Agg-2 polypeptide, such as a propeptide domain, a catalytic domain, a disintegrin-like domain, a trombospondin type-1 domain, a cysteine-rich domain, a spacer domain, or a combination thereof.

An aggrecanase polypeptide can have an active site. For example, the catalytic domain is an active site of an aggrecanase. In general, an active site can include a site of ligand binding, or a site of phosphorylation, glycosylation, alkylation, acylation, or other covalent modification. A site of ligand binding can be a site of aggrecan binding or a site of binding of an agonist or antagonist. An active site can include an attachment site for a sulfated glycosaminoglycan, such as a chondroitin sulfate and keratin sulfate, or a site of protease cleavage such as a furin cleavage site. The active site can interact with a component of the extracellular matrix, such as a heparin or an integrin. A ligand binding site can include accessory binding sites adjacent to or proximal to the actual site of binding that may affect activity upon interaction with the ligand. An active site of the human Agg-1 polypeptide can include amino acids of SEQ ID NO:1 or SEQ ID NO:2 (FIG. 1A or FIG. 1B, respectively). For example, an active site of the human Agg-1 polypeptide can include one or more of amino acids Leu330, Gly331, Ala333, His361, Phe357, and Ala248 as defined by the amino acid positions of SEQ ID NO:1 and SEQ ID NO:2. An active site of the human Agg-2 polypeptide can include amino acids of SEQ ID NO:3 (FIG. 3). For example, an active site of the human Agg-2 polypeptide can include one or more of amino acids Glu411, Asp377, Leu379, Ser441, and Leu443 as defined by the amino acid positions of SEQ ID NO:3 (FIG. 3).

The numbering of the amino acids of the human Agg-1 polypeptide or the human Agg-2 polypeptide may be different than that set forth herein, and the sequence of the human Agg-1 polypeptide or the human Agg-2 polypeptide may contain certain conservative amino acid substitutions that yield the same three-dimensional structure. For example, the numbering of the human Agg-1 polypeptide may be different than that set forth in FIG. 1A or FIG. 1B, and the sequence of the human Agg-1 polypeptide may contain conservative amino acid substitutions but yield the same structure as that defined by the coordinates of Tables 4 and 5 and illustrated in FIGS. 2, 5, 6, 10, and 11. The numbering of the human Agg-2 polypeptide may be different than that set forth in FIG. 3, and the sequence of the human Agg-2 polypeptide may contain conservative amino acid substitutions but yield the same structure as that defined by the coordinates of Table 6 and illustrated in FIG. 8. Corresponding amino acids and conservative substitutions in other isoforms or analogs are easily identified by visual inspection of the relevant amino acid sequences or by using commercially available homology software programs (e.g., MODELLAR, MSI, San Diego, Calif.).

An analog is a polypeptide having conservative amino acid substitutions. A conservative substitution can include switching one amino acid for another with similar polarity, steric arrangement, or of the same class (e.g., hydrophobic, acidic or basic), and includes substitutions having an inconsequential effect on the three-dimensional structure of the human Agg-1 polypeptide or the human Agg-2 polypeptide with respect to identification and design of agents that interact with the polypeptide, as well as for molecular replacement analyses and/or for homology modeling.

An aggrecanase polypeptide, such as an Agg-1 polypeptide and an Agg-2 polypeptide, can originate from a nonmammalian or mammalian species. A mammalian aggrecanase polypeptide can originate from a human, for example. Exemplary nonhuman mammals include a nonhuman primate (such as a monkey or ape), a mouse, rat, goat, cow, bull, pig, horse, sheep, wild boar, sea otter, cat, and dog. Exemplary nonmammalian species include chicken, turkey, shrimp, alligator, and fish.

An agent can be, for example, a chemical compound (e.g., a polypeptide, nucleic acid, peptidomimetic). A peptidomimetic is a chemical compound that can mimic the ability of a peptide to recognize certain physiological molecules, such as proteins and nucleic acids. In some instances, the peptidomimetic includes non-peptidic structural elements that are capable of mimicking or antagonizing the biological action(s) of a natural parent peptide. For example, scissile peptide bonds can be replaced with one or more non-scissile dipeptide isosteres.

In general, agents that interact with an Agg-1 polypeptide may also interact with an Agg-2 polypeptide, and agents that interact with an Agg-2 polypeptide may also interact with an Agg-1 polypeptide. For example, the compositions and methods described herein would be appropriate for use when Compound 1 is bound to an Agg-2 polypeptide, and when batimastat is bound to an Agg-1 polypeptide.

While embodiments have been described in which Compound 1 or batimastat is a ligand, more generally other compounds may also be used as ligands.

As an example, based on a representation of the human Agg-1 polypeptide bound to Compound 1, derived from the structure of the crystalline complexes, and without wishing to be bound by theory, it is believed that a Zn atom in the active site chelates with one of the carboxylate oxygen atoms of Compound 1 at a distance of about 2.1 Å (see FIG. 12), and that the other carboxylate oxygen participates in a water-mediated hydrogen bond with the backbone atoms of Ala333. It is also believed, however, that this water-mediated interaction is present only in the mutant form of the protein. It is further believed that carboxylate MMP inhibitors generally bind more favorably when protonated because they can form a direct hydrogen bond with the carboxylate of the active site Glu (Glu362), which was replaced with Gln in the mutant crystallized protein (compare FIGS. 1A and 1B). In the mutant crystallized protein, a primary amide replaced the carboxylate (via the Glu->Gln mutation), and it is therefore believed that the water-mediated hydrogen bond could not be made. Thus, the second oxygen of Compound 1 is believed to have been free to interact with other portions of the protein. It is believed that a second area of interaction between Compound 1 and the human Agg-1 polypeptide is at the site of a hydrogen bond acceptor near the zinc atom within the human Agg-1 polypeptide. It is also believed that one of the oxygen atoms from the sulfonamide of Compound 1 occupies this area through interactions with the backbone NHs of both Leu330 and Gly331, at distances of 2.7 Å and 3.1 Å, respectively. It is further believed that the S1' pocket of the active site, which spans about 15 Å, is filled by the substituted bi-phenyl portion of Compound 1. In addition, it is believed that within the S1' pocket are favorable π stacking interactions between the biphenyl moiety and His361 of the Agg-1 active site (having about 3.7 Å separation). It is believed that an additional favorable π stacking interaction occurs between the phenyl moiety substituted on the biphenyl and Phe357. It is also believed that the carbonyl moiety, which is a substituent on the phenyl moiety, forms a water mediated (2.5 Å) hydrogen bond with the backbone atoms of αB.

Based on this information, and without wishing to be bound by theory, it is believed that other compounds capable of having one or more similar interactions with a human Agg-1 polypeptide may also be capable of acting as ligands for the human Agg-1 polypeptide. Such compounds may have the structure:

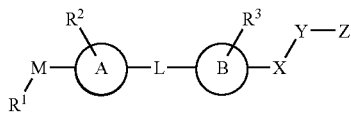

where each A and B represent a ring (e.g., a cyclyl ring, a heterocyclyl ring, an aryl ring, or a heteroaryl ring), each L, M, and Y are linker moieties, each $R^1$, $R^2$, and $R^3$ are substituents, X is a hydrogen bond acceptor, and Z is a metal chelating moiety.

In general, each A and B is independently formed of at least five atoms (e.g., five atoms, six atoms, seven atoms, eight atoms, nine atoms, 10 atoms, 11 atoms, 12 atoms, 13 atoms, 14 atoms). One or more atoms (e.g., one atom, two atoms, three atoms, four atoms) can independently be heteroatoms (e.g., N, S, O). For example, in some embodiments, each A and B is independently aryl or heteroaryl moieties. Examples of such aryl and heteroaryl moieties include phenyl, pyridyl, pyrimidyl, pyridazyl, thiophenyl, furanyl, and pyrrolyl.

In some embodiments, each L and M can be a bond, for example, providing a direct attachment of A with B. In certain embodiments, each L and M can independently provide a spacer, for example a one or two atom spacer, between the two moieties linked together. Examples of such linkers include methylene, ethylene, oxygen, sulfur, amino, methyleneoxy, methyleneamino, methylenethioyl, sulfoxide, or sulfone.

Y is generally a moiety linking the hydrogen bond acceptor, X, to the metal chelator, Z. In some embodiments, Y is a linker. Examples of linkers include alkyl linkers, such as alkyl linkers having a branched side chain (e.g., an isopropyl side chain). Additional examples of linkers include alkylene linkers (e.g., methylene, ethylene, propylene, isopropylene, butylene, or isobutylene), oxygen, sulfur, amino linkers, methyleneoxy, methyleneamino, methylenethioyl, sulfoxide and sulfone. In some embodiments, Y is a bond.

Figure 12:
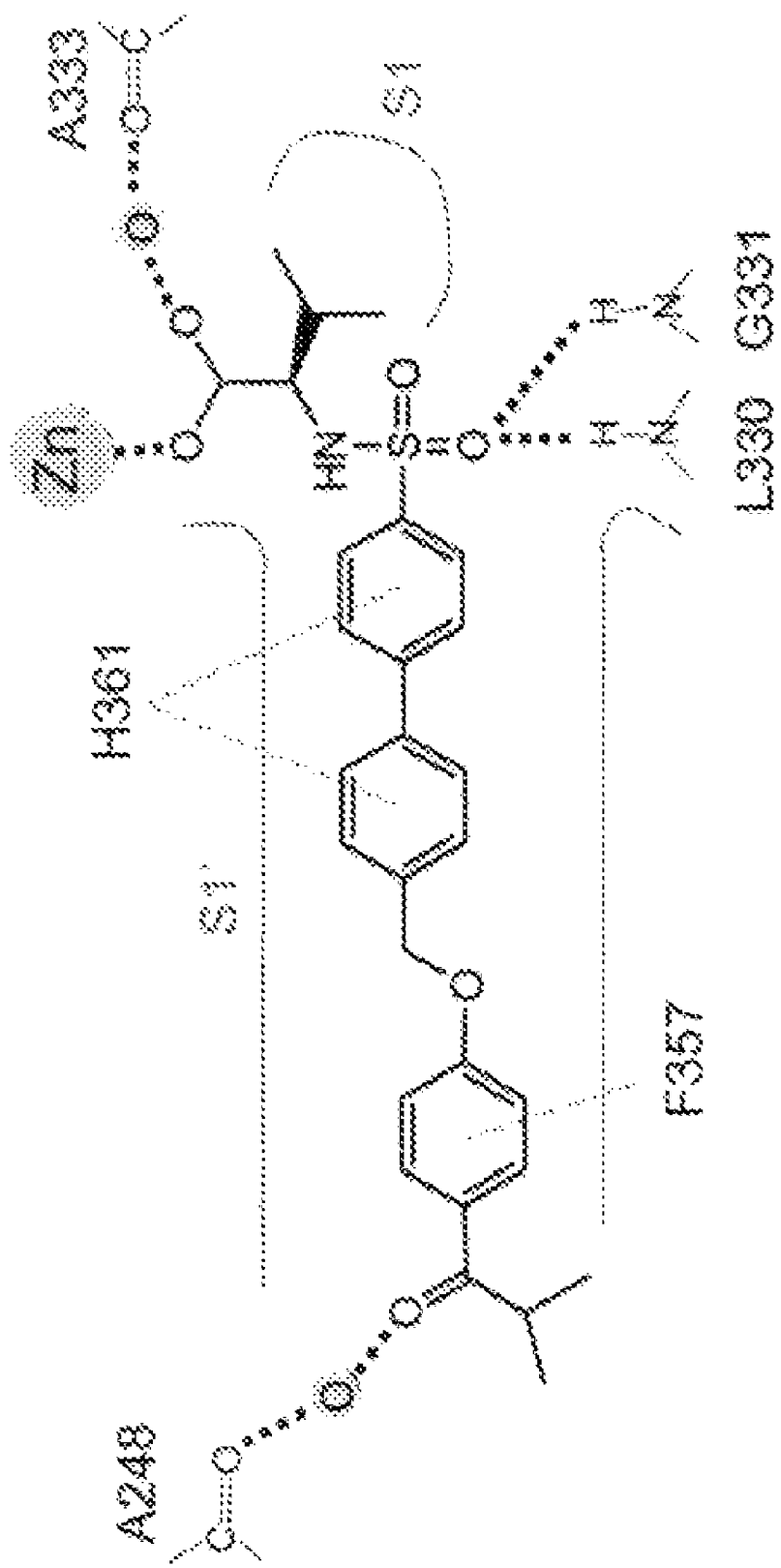
FIG. 12 is the structure of the inhibitor Compound 1. Interactions between Compound 1 and the Agg-1-A1C2 polypeptide, and the active zinc atom are indicated. S1 and S1' represent successive substrate binding pockets.

$R^1$ is generally a moiety on the A ring that can extend into the S1' pocket of the human Agg-1 polypeptide (see FIG. 12, for example). In some embodiments, $R^1$ is H. In certain embodiments, $R^1$ is a larger moiety that extends more deeply into the S1' pocket. As an example, in some embodiments, $R^1$ is a $C_1$-$C_6$ alkyl (e.g., $C_1$ alkyl, $C_2$ alkyl, $C_3$ alkyl, $C_4$ alkyl, $C_5$ alkyl, $C_6$ alkyl), $C_2$-$C_6$ alkenyl (e.g., $C_1$ alkenyl, $C_2$ alkenyl, $C_3$ alkenyl, $C_4$ alkenyl, $C_5$ alkenyl, $C_6$ alkenyl) or $C_2$-$C_6$ alkynyl (e.g., $C_1$ alkynyl, $C_2$ alkynyl, $C_3$ alkynyl, $C_4$ alkynyl, $C_5$ alkynyl, $C_6$ alkynyl). As another example, in certain embodiments $R^1$ is a ring moiety, such as a cyclyl ring, a heterocyclyl ring, an aryl ring, or a heteroaryl ring. In some embodiments, $R^1$ is a fused ring system, for example, a fused cylcyl, aryl, heterocyclyl or heteroaryl ring system. In some embodiments, one or more heteroatoms in the heterocyclyl or heteroaryl ring system participates in a hydrogen bond (e.g., a water mediated hydrogen bond) with the peptide backbone of Ala248. In some embodiments, $R^1$ is substituted. In certain embodiments, one or more of the substituents can participate as a hydrogen bond acceptor with the carbonyl backbone of Ala248 (e.g., via a water molecule). For example, the substituents can be nitro, cyano, alkylcarbonyl, sulfoxide, sulfone, sulfonamide, carbonyl, carboxamide, carbamate, or carbonate.

In general, each $R^2$ and $R^3$ is independently, a neutral substituent including less than about eight non-hydrogen atoms. A neutral substituent has no net positive or negative charge. Examples of such substituents include hydrogen, halogen (e.g., F, Cl, Br), OC(halogen)$_3$, C(halogen)$_3$, $C_1$-$C_6$ alkoxy (e.g., $C_1$ alkoxy, $C_2$ alkoxy, $C_3$ alkoxy, $C_4$ alkoxy, $C_5$ alkoxy, $C_6$ alkoxy), $C_1$-$C_6$ alkyl (e.g., $C_1$ alkyl, $C_2$ alkyl, $C_3$ alkyl, $C_4$ alkyl, $C_5$ alkyl, $C_6$ alkyl), $C_1$-$C_6$ alkylthioyl (e.g., $C_1$ alkylthioyl, $C_2$ alkylthioyl, $C_3$ alkylthioyl, $C_4$ alkylthioyl, $C_5$ alkylthioyl, $C_6$ alkylthioyl), or $C_1$-$C_6$ alkylamino (e.g., $C_1$ alkylamino, $C_2$ alkylamino, $C_3$ alkylamino, $C_4$ alkylamino, $C_5$ alkylamino, $C_6$ alkylamino). In some embodiments, $R^2$ and $R^3$, taken together with the ring atom to which they are attached, form a ring (e.g., providing a fused three ring system with A and B). For example $R^2$ and $R^3$, taken together with the atoms of attachment from A and B can form a cyclyl ring, a heterocyclyl ring, an aryl ring, or heteroaryl ring. In some embodiments, the neutral substituent is hydrophobic.

X is generally a hydrogen bond acceptor. Examples of hydrogen bond acceptors include sulfur, sulfoxide, sulfone, sulfonamide, carbonyl, carboxamide, urea, carbamate and carbonate.

Z is generally a metal chelating moiety. For example, Z can be a bidentate metal chelator that can chelate with a metal such as Fe, Mg, Mn, or Zn. Examples of metal chelating moities include carboxylic acid, carboxylic amide, hydroxamic acid (for example a reverse hydroxamic acid), hydroxyurea, hydrazide, sulfonic acid, sulfonamide, hydroxysulfonamide, sulfodiimide, phosphoric acid, phosphonic acid, thiol, thiol carbonyl, thiirane, dithiol, sulfonylhydrazide, a heterocyclic moiety (e.g., sulfodiimine, thiazoladine dione, pyrimidine trionethiadiazine, barbiturate, thiadiazole (e.g., a peptidic thiadiazole or thiadiazolethione), thiadiazine, imidazolidinedione, pryidinione, aminomethyl benzimidazole) napthylhydroxamate, or a heterocyclic moiety bound to an amide or carbonyl moiety (e.g., pyridinylamide, pyridinylone, or pyrrolylone).

As another example, based on a representation of the human Agg-2 polypeptide bound to batimastat, derived from the structure of the crystalline complexes, and without wishing to be bound by theory, it is believed that the hydroxamate moiety of batimastat interacts with both the active site metal (having, for example, O—Zn distances of 2.1 Å and 2.6 Å) and the carboxylate sidechain of the catalytic glutamic acid (Glu411 of Agg-2) via hydrogen bonding (O—O distance of 2.4 Å). It is also believed that the peptidomimetic inhibitor batimastat interacts with the human Agg-2 polypeptide in an extended, beta-sheet-like conformation. It is further believed that the three sidechains of batimastat (thiophene, isobutyl, and benzyl) interact with successive substrate binding pockets, while the two backbone amide groups make four beta-sheet-like hydrogen-bonds with the protein. In addition, it is believed that the thiophene, isobutyl, and benzyl sidechains occupy the S1, S1', and S2' sites respectively, while the intervening amide moieties form hydrogen bonds to the backbone atoms of Asp377, Leu379, Ser441, and Leu443. It is believed that the heavy atom distances of these hydrogen bonds are 2.8 Å, 3.1 Å, 2.7 Å, and 2.7 Å, respectively.

Based on this information, and without wishing to be bound by theory, it is believed that other compounds capable of having one or more similar interactions with a human Agg-2 polypeptide may also be capable of acting as ligands for the human Agg-2 polypeptide. Such compounds may have the structure:

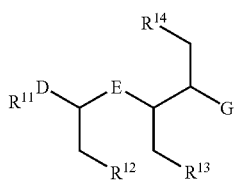

where each of D and E represent an amide bond or other bond, each of $R^{11}$, $R^{12}$, $R^{13}$, and $R^{14}$ represent side chain moieties, for example side chains in the naturally occurring amino acids or side chains found in unnaturally occurring or artificial amino acids; and G is a metal chelating moiety.

In some embodiments, each D and E is independently amide, sulfonamide, aminomethylenehydroxyl, carbamate, carbonate, vinyl, or urea.

Figure 13:
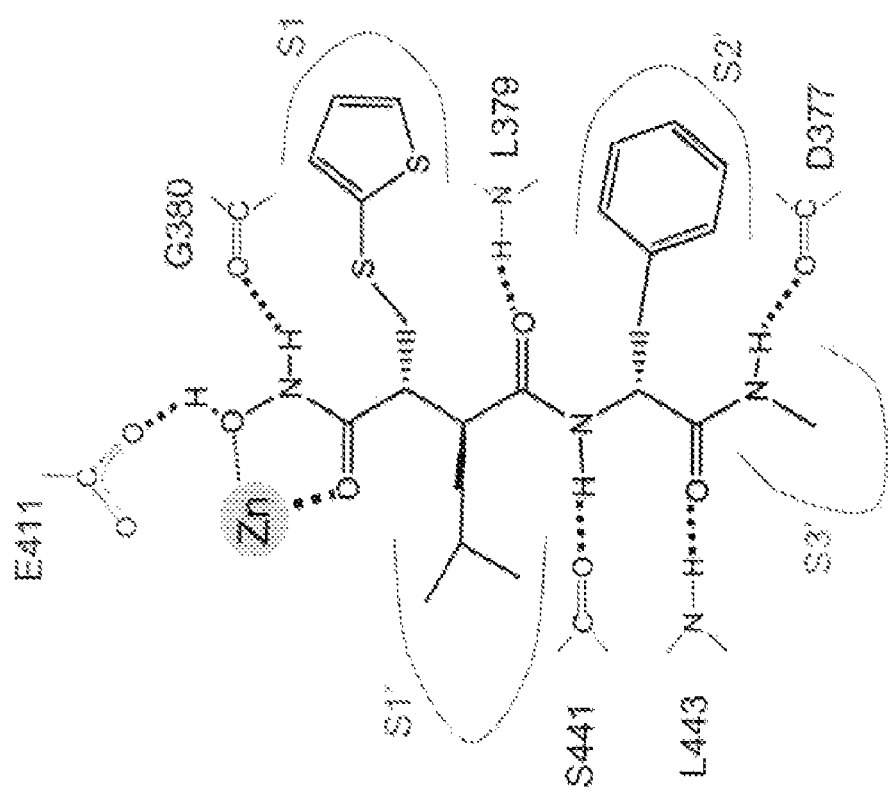
FIG. 13 is the structure of batimastat. Interactions between batimastat and amino acid residues of the human Agg-2 polypeptide (SEQ ID NO:3) and the active site zinc atom are indicated. S1, S2', S3' and S1' represent successive substrate binding pockets.

In general, each of $R^{11}$, $R^{12}$, $R^{13}$, and $R^{14}$ is sized and shaped to fill pockets S3', S2', S1', and S1 of the human Agg-2 polypeptide, respectively (see FIG. 13, for example). For example, the S3' pocket is relatively small, and therefore, in some embodiments, $R^{11}$ is a lower alkyl, such as, for example, a hydrogen, or preferably a methyl, ethyl, or propyl. Each of pockets S2', S1' and S1 are slightly larger than S3' and therefore can accommodate larger side chain moieties. Accordingly, in some embodiments, each of $R^{12}$, $R^{13}$, and $R^{14}$ is independently a neutral moiety, such as, for example a ring moiety, a chain moiety, or a combination of a ring and chain moiety. For example, each of $R^{12}$, $R^{13}$, and $R^{14}$ can be independently $C_1$-$C_6$ alkyl (e.g., $C_1$ alkyl, $C_2$ alkyl, $C_3$ alkyl, $C_4$ alkyl, $C_5$ alkyl, $C_6$ alkyl), $C_2$-$C_6$ alkenyl (e.g., $C_1$ alkenyl, $C_2$ alkenyl, $C_3$ alkenyl, $C_4$ alkenyl, $C_5$ alkenyl, $C_6$ alkenyl) or $C_2$-$C_6$ alkynyl (e.g., $C_1$ alkynyl, $C_2$ alkynyl, $C_3$ alkynyl, $C_4$ alkynyl, $C_5$ alkynyl, $C_6$ alkynyl), cyclyl, heterocycly, aryl, heteroaryl cyclyloxy, heterocyclyoxy, aryloxy, heteroaryloxy, cyclylthio, heterocyclythio, arylthio, heteroarylthio, cyclylalkyl, heterocyclylalkyl, arylalkyl, or heteroarylalkyl. In some embodiments, $R^{12}$ is an aryl moiety (e.g., a phenyl moiety). In some embodiments, $R^{13}$ is an alkyl moiety (e.g., an isopropyl moiety). In some embodiments, $R^{14}$ is a heteroarylthio moiety (e.g., a thiophenylthio moiety). In some embodiments, the neutral moiety is a hydrophobic moiety.

As described above, generally, G is a metal chelating moiety. For example, G can be a bidentate metal chelator that can chelate with a metal such as Fe, Mg, Mn, or Zn. In some instances, G can also participate in hydrogen bonding with the hydrogen bond acceptor near the catalytic metal (e.g., catalytic Zn) of the human Agg-2 polypeptide. In some embodiments, this hydrogen bond acceptor can stabilize the substrate through an amide carbonyl in the peptide backbone. Examples of metal chelating moieties include carboxylic acid, carboxylic amide, hydroxamic acid (e.g., a reverse hydroxamic acid), hydroxyurea, hydrazide, sulfonic acid, sulfonamide, hydroxysulfonamide, sulfodiimide, phosphoric acid, phosphonic acid, thiol, thiol carbonyl, thiirane, dithiol, sulfonylhydrazide, a heterocyclic moiety (e.g., sulfodiimine, thiazoladine dione, pyrimidine trionethiadiazine, barbiturate, thiadiazole (e.g., a peptidic thiadiazole or a thiadiazolethione), thiadiazine, imidazolidinedione, pyridinione, aminomethyl benzimidazole), napthylhydroxamate, or a heterocyclic moiety bound to an amide or carbonyl moiety (e.g., pyridinylamide, pyridinylone, or pyrrolylone).

It is believed that a ligand having the structures described above can have a physiological effect similar to Compound 1 or batimastat. For example, it is believed that the ligand can inhibit cleavage of aggrecan.

The following examples are illustrative and not intended as limiting.

EXAMPLES

Example 1

Agg-1-A1C2 and Agg-1-A1C2 Bound to Compound 1 were Crystallized and their Structures Determined A mutant form of a recombinant human Agg-1 polypeptide was cloned into a vector for expression in Chinese Hamster Ovary (CHO) cells. The construct encoded the A1C2 mutant Agg-1 (hereafter, Agg-1-A1C2), which carried a glutamine at amino acid position 362 instead of a glutamate (FIG. 1A), was stable against proteolysis, appeared more amenable to crystallization than the wildtype counterpart, and had specificity and inhibitor sensitivity similar to those of the full-length wildtype protein.

To express selenomethionine labeled Agg-1-A1C2, CHO cells were grown in 175 cm² flasks containing 75 ml of the maintenance medium (R1 medium buffered with 10 mM Hepes, pH 7.3, 1.25 mg/L Fungizone, 10% dialyzed and heat-inactivated Fetal bovine serum, 1% Penicillin/Streptomycin, 2 mM Glutamine, 0.5 g/L G418, 50 nM Methotrexate) in a humidified incubator with 5% $CO_2$ at 37° C. Then 2.5× $10^7$ cells were transferred to a 1700 cm² roller bottle containing 400 ml of the maintenance medium. Cells were grown at 37° C. with slow rolling in a Bellco machine (Bellco Glass, Inc., Vineland, N.J.).

When the cells reached >90% confluence, the medium was discarded and the roller bottle was washed twice with phosphate-buffered saline. The cells were labeled with selenomethionine at 37° C. with slow rolling in 300 ml of the labeling medium (Methionine-free DME medium with 1.25 mg/L Fungizone, 1% Penicillin/Streptomycin, 2 mM Glutamine, 30 mg/L selenomethionine, 50 mg/L Heparin, 0.5 g/L G418, 50 nM Methotrexate) for 4 days. After labeling, the medium was harvested, filtrated, and stored at −80° C. The cells remaining in the roller bottle were further cultured in 300 ml of fresh labeling medium for 3 days at 37° C. The medium was then harvested, filtrated and stored at −80° C. A total of 10 liters of conditioned media containing the secreted selenomethionine-labeled human Agg-1 polypeptide were prepared. The expression level was estimated to be 1 mg/L. Mass spectrometry indicated >90% selenium incorporation in the labeled proteins.

Conditioned CHO media expressing the Agg-1-A1C2 construct was diluted into 25 mM Hepes pH 6.8, 5 mM $CaCl_2$, 10 $\mu$M $ZnCl_2$, bound to a Poros® HQ column (Applied Biosystems, Foster City, Calif.) and eluted with linear gradient 50 mM-1M NaCl. Agg-1-A1C2-containing fractions were loaded onto a polypropyl aspartamide hydrophobic interaction column (Nest Group, Southborough, Mass.) in 1.2 M $(NH_4)_2SO_4$. Agg-1-A1C2 was eluted by decreasing $(NH_4)_2SO_4$ concentration. Subsequent purification steps included gel filtration (G3000SW) and anti-Flag M2 affinity chromatography. The unbound material from the Flag affinity column was bound to a Mono Q column (Pharmacia) using starting buffer 25 mM MMT pH 6.8, 50 mM NaCl and elution with a linear gradient up to 1M NaCl. Protein was dialyzed into final buffer consisting of 25 mM Hepes pH 6.8, 5 mM $CaCl_2$, 10 $\mu$M $ZnCl_2$, 300 mM NaCl. All purification steps were performed at 4° C.

The Agg-1-A1C2 protein was concentrated to 8 mg/mL in 25 mM HEPES pH 6.8, 300 mM NaCl, 10 $\mu$M $ZnCl_2$, 5 mM $CaCl_2$. The Agg-1-A1C2/Compound 1 complex was obtained by incubating the protein with 1.2 molar excess of the inhibitor. Crystals of unliganded Agg-1-A1C2 and the Agg-1-A1C2/Compound 1 complex were grown by hanging drop technique at 18° C. using 10% PEG 4K, 0.1 M MES pH 6.0 as a precipitating solution. Optimized crystals were obtained by streak seeding and macro seeding with an addition of 8-15 mM L-cysteine. Crystals grew to a maximum size of 0.4×0.4× 0.2 mm³ in about 2-3 weeks. Crystals from the selenomethione substituted Agg-1-A1C2 protein were grown using the same technique, as described above. Crystals of inhibitor-bound protein belong to the monoclinic space group $P2_1$ and have unit cell parameters a=82.566 Å, b=82.618 Å, c=99.326 Å, β=90.626°, with 4 molecules per crystallographic asymmetric unit. Unliganded protein crystallized in the space group $P2_1$ with unit cell parameters a=128.28 Å, b=83.63 Å, c=150, 16 Å, β=112.409°, and with 8 molecules per asymmetric unit. For data collection crystals were transferred to the solution containing the crystallization reagent plus 25% glycerol, and then flash-frozen in the liquid nitrogen at 100K.

The structure of inhibitor-bound Agg-1-A1C2 was determined with phases obtained by multiwavelength anomalous diffraction (MAD) from crystals of selenomethionine-substituted protein. MAD data were collected at three wavelengths on beam line 5.0.2 at the Advanced Light Source, Berkeley, Calif., using a Quantum-4 CCD detector (Area Detector Systems). The data were integrated with MOSFLM and then scaled with SCALA ("The CCP4 Suite: Programs for Protein Crystallography," *Acta Crystallogr*. Sect. D 50:760-763, 1994). Selenium sites were located using SHELXS. Refinement of anomalous scatterer parameters, phase calculation and density modification by SOLOMON, and all were performed with SHARP (de La Fortelle and Brigogne, *Methods Enzym*. 276:472-494, 1997). Experimental maps were used to build an initial model (QUANTA), with subsequent rounds of rebuilding and refinement in CNS (Brunger et al., *Acta Crystall*. Sect D 54:905-921, 1997) against native data. The 2.8 Å native data set was collected at the Advanced Light Source, processed with MOSFLM and scaled with SCALA ("The CCP4 Suite: Programs for Protein Crystallography," *Acta Crystallogr*. Sect. D 50:760-763, 1994). Statistics for data collection, phasing and refinement for the Agg-1-A1C2/Compound 1 complex are summarized in Table 1.

TABLE 1

Statistics of X-Ray Diffraction Data Collection for Agg-1-A1C2/Compound 1

| | Multiwavelength Anomalous Diffraction | | | |
|---|---|---|---|---|
| | Peak | Inflection | Remote | Native |
| Data | | | | |
| Wavelength (Å) | 0.9794 | 0.9795 | 0.9649 | 1.0 |
| Resolution (Å) | 2.8 | 2.8 | 2.95 | 2.8 |
| No of Reflections | 31,810 | 31,820 | 27,055 | 33,154 |
| I/σ(I) | 7.9 (1.6) | 7.1 (1.4) | 6.1 (1.6) | 6.5 (1.8) |
| Completeness (%) | 96.2 | 96.2 | 95.8 | 100 |
| Redundancy | 4.8 | 4.8 | 4.8 | 4.0 |
| Rsym (%) | 9.3 (47) | 10.3 (57) | 12.1 (48) | 8.3 (41) |
| Crystal System | | Monoclinic | | Monoclinic |
| Space Group | | $P2_1$ | | $P2_1$ |
| Unit Cell | | a = 82.07 Å | | a = 82.57 Å |
| | | b = 83.96 Å | | b = 82.62 Å |
| | | c = 98.95 Å | | c = 99.33 Å |
| | | β = 89.9° | | β = 90.6° |
| Molecules per Asymmetric unit | | 4 | | 4 |

TABLE 1-continued

Statistics of X-Ray Diffraction Data Collection for Agg-1-A1C2/Compound 1

| | Multiwavelength Anomalous Diffraction | | | |
|---|---|---|---|---|
| | Peak | Inflection | Remote | Native |
| Phasing | | | | |
| FOM (acen/cen) | | 0.359/0.245 | | |
| PhP anom | 0.88 | 0.632 | 0.273 | |
| PhP iso (acen/cen) | | 0.398/0.34 | 0.486/0.38 | |
| Refinement | | | | |
| Number of reflections (free) | | | | 31,491 (1,646) |
| Rwork (%) | | | | 22.6 |
| Rfree (%) | | | | 26.9 |
| No. of protein atoms | | | | 8,595 |
| No. of waters | | | | 46 |
| RMSD from ideal geometry | | | | |
| Bonds (Å) | | | | 0.008 |
| Angles (°) | | | | 1.43 |

Radiation Source: Quantum 4 CCD Area Detector at ALS (Berkeley, Calif.)

The structural coordinates of the refined model of the Agg-1-A1C2/Compound 1 complex are presented below in Table 5. In Table 5, the "#" column assigns an index to each atom for which coordinates are given. The "name" column indicates what type of atom, and the "res" column indicates what type of residue the atom belongs to. The "chain" indicates which polypeptide the atom belongs to. "Res #" gives the residue number for the atom. For example, atom number 1 (the first row in Table 5) is the beta carbon (CB) of Ala214. Its x, y, and z structural coordinates are given in the X, Y, and Z columns, respectively. The column headed "occ" describes the occupancy assigned to the atom (1.00=full occupancy), and the "B" column provides B factors (or temperature factors) in units of Å$^2$. Coordinates of bound Compound 1 are denoted with the entry "WAY" in the res column, water is denoted by "HOH," and zinc and calcium atoms are denoted by "ZN" and "CA," respectively.

Subsequently, the crystal structure of the unliganded form of the Agg-1-A1C2 was solved by molecular replacement method with AMORE ("The CCP4 Suite: Programs for Protein Crystallography," *Acta Crystallogr.* Sect. D 50:760-763, 1994) and CNS (Brunger et al., *Acta Crystallogr.* Sect. D 54:905-921, 1997), using the refined structure of the inhibitor-bound form. Diffraction data from crystals of unliganded enzyme were collected to 3 Å resolution at the Advanced Light Source, and processed and reduced with MOSFLM and SCALA ("The CCP4 Suite: Programs for Protein Crystallography," *Acta Crystallogr.* Sect. D 50:760-763, 1994). Statistics for data collection and refinement are shown in Table 2.

The structural coordinates of the refined model of the Agg-1-A1C2 polypeptide are presented below in Table 4. The columns and designations of Table 4 are as described for Table 5.

TABLE 2

Statistics of X-Ray Diffraction Data Collection for Agg-1-A1C2

| | |
|---|---|
| Crystal System | Monoclinic |
| Space Group | P2$_1$ |
| Unit Cell Dimensions | a = 128.28 Å, b = 83.63 Å, c = 150.16 Å, β = 112.409° |
| Data Collection Temperature | |
| Number of crystals | 1 |
| Radiation Source | Quantum 4 CCD area detector at ALS (Berkeley, CA) |

TABLE 2-continued

Statistics of X-Ray Diffraction Data Collection for Agg-1-A1C2

| | |
|---|---|
| X-ray wavelength | 1.0 Å |
| Resolution range of data | 30.0-3.0 Å |
| Maximum Resolution | 3.0 Å |
| R$_{merge}$$^a$ | 12% (51%) |
| Completeness | 96.0% |
| Redundancy | 5.6 |
| Total reflections | |
| Unique reflections | |
| No. reflections/free (F/σ(F) > 2) | 40,190/2,160 |
| I/σ(I) | 6.5 (1.8) |
| Phasing and Refinement | |
| Model for molecular refinement | Agg-1-A1C2/ Compound 1 complex |
| Construct (amino acids) | Agg-1-A1C2 |
| Compounds (ligands) | None |
| Agg-1-A1C2 molecules per asymmetric unit | 8 |
| Resolution range of refinement | 30.0-3.0 Å |
| R$_{work}$$^b$ | 25.2% |
| R$_{free}$$^c$ | 29.0% |
| Number of non-hydrogen protein atoms | 8,595 |
| Number of water molecules | 90 |
| RMS deviations from ideal bond lengths | 0.008 |
| RMS deviations from ideal bond angles | 1.56 |

$^a$R$_{merge}$ = |I$_h$ − <I$_h$>|/I$_h$, where <I$_h$> is the average intensity over symmetry equivalents.
$^b$R$_{work}$ = ||F$_{obs}$| − |F$_{calc}$||/F$_{obs}$|
$^c$R$_{free}$ is equivalent to R$_{work}$, but calculated for a randomly chosen 5% of reflections omitted from the refinement process.

The structure of the Agg-1-A1C2/Compound 1 complex is shown in FIG. 5. The N-terminal residues 214-428 represent the catalytic domain of the enzyme, and the C-terminal residues 438-509 represent the disintegrin-like domain. The two domains are connected by a 9-residue crossover linker (residues 429-438) that extends across the surface of the catalytic domain on the side opposite to the zinc-binding region.

The catalytic domain of Agg-1-A1C2 reveals a characteristic polypeptide fold that shares structural features with the zinc-peptidase superfamily. It has an α/β structure consisting of six α-helices (αA-αF) surrounding a core of five β-strands (βA-βE) and topologically is more similar to snake venom metalloproteinases (SVMP) than to MMPs. The catalytic zinc environment involves the characteristic zinc-chelating motif $^{361}$HExxHxxxxxH$^{371}$ (SEQ ID NO: 4) with three histidines (His361, His365 and His371) coordinating the zinc atom and the Met-turn motif $^{390}$xMx$^{392}$ with the invariant methionine (Met391) essential for the structural integrity of the zinc-binding site. Compared with SVMPs and MMPs that share a conserved glycine residue in the zinc-binding region (HExx-HxxGxxH (SEQ ID NO: 5)), the topologically equivalent asparagine (Asn368) in Agg-1-A1C2 is arranged in a similar conformation to allow for a sharp turn in the polypeptide chain. Accommodation of glutamine residue (Gln362) in place of the catalytic glutamic acid (Glu362) has no effect on the architecture of the active site.

As shown in more detail in FIG. 6, in contrast to SVMPs that have a range of one- to three-disulfide bonds, this structural arrangement is supported by four disulfide bridges formed between cysteines that are conserved in the ADAMTS family: Cys293-Cys345, Cys322-Cys327, Cys339-Cys423 and Cys377-Cys407. Among these, the Cys339-Cys423 disulfide connection has a structural equivalent in the SVMP structures, but the others seem to be unique to aggrecanases. The Cys293-Cys345 bridge anchors the long αC helix (Cys293) to the β-sheet (Cys345), the Cys322-Cys327 disulfide keeps together sequentially distant parts of the S-shaped loop (S-loop, MMP terminology) and the Cys377-Cys407 connection locks the small αE helix (Cys377) against the C-terminal helix αF (Cys407). In addition, there are three calcium ions, identified by large peaks in the electron density. One $Ca^{2+}$ ion is found near the Cys322-Cys327 disulfide bridge, forming contacts to three carbonyl oxygens (Leu321, Cys327, Thr329) and three carboxylate oxygens (Asp320, Glu349). Another site, harboring two calcium ions, is in the vicinity of the Cys339-Cys423 bridge, in a location similar to the calcium-binding site in SVMPs. However, in Agg-1-A1C2 this region reveals a highly charged environment that allows for two calcium ions as opposed to the one in SVMPs structures, such as the structures described for atrolysin C and adamalysin II. The two $Ca^{2+}$ ions are separated by 4.3 Å and collectively are coordinated with three aspartates (Asp304, Asp311, Asp426), one glutamate (Glu221) and two carbonyl groups (Asp304, Cys423). Comparative amino acid sequence analysis with the Agg-1-A1C2 structure indicates that the residues coordinating the calcium ions at both sites have a high level of conservation across the aggrecanase family.

The disintegrin-like domain of Agg-1-A1C2 is made up of two small α-helices followed by two highly twisted antiparallel β-sheets. Each β-sheet has three short β-strands interrupted by irregular connections and long loops. This arrangement is held in place by four disulfide bridges between eight conserved cysteines, as shown in FIG. 8: Cys449-Cys472, Cys460-Cys482, Cys467-Cys501, Cys495-Cys506. The orientation of this domain is maintained by a number of electrostatic and hydrophobic interactions within the catalytic domain.

The active site of Agg-1 is very similar to that of the MMPs and SVMPs (Rush and Powers, *Current Topics in Med. Chem.* 4:1311-1327, 2004). In general, the active site is broadly defined by a narrow concave groove on the surface of the catalytic domain that runs parallel to βD. At the center of this groove is the catalytic Zn, which is key to protease activity as it activates the water molecule responsible for hydrolysis of the substrate's peptide bond. As indicated above, the nitrogen atoms of Histidines 361, 365 and 371 coordinate the catalytic Zn of Agg-1. Also common to other protease active sites are the presence of several inward-facing pockets and solvent facing grooves adjacent to the major active site groove. These features of the protein accommodate the sidechains of the substrate and are thus useful to discriminate against sidechains for selectivity. Finally, a hydrogen bond acceptor "hot spot" near the catalytic Zn may stabilize the substrate through a hydrogen bond with one of the protein's amide carbonyls. In Agg-1, this "hot spot" is located at a tight turn in the backbone preceding βD and is formed by the two inward facing backbone NHs of Leu330 and Gly331.

Most known inhibitors of MMPs and SVMPs share several features. The first is a Zn-chelating group that occupies the fourth coordination site of the active site Zn atom. This interaction contributes a significant amount of energy to the free energy of binding. The same interaction is observed for the inhibitor described here within, which chelates the Zn via one of the carboxylate oxygen atoms at a distance of 2.1 Å. The other carboxylate oxygen is participating in a water-mediated hydrogen bond with the backbone atoms of Ala333. Carboxylate MMP inhibitors are known to bind more favorably when protonated, because they can form a direct hydrogen bond with the carboxylate of the active site Glu (Glu362 in Agg-1). Therefore, we predict that the water-mediated interaction with Ala333 is only present in the mutant form of the protein. Since in Agg-1-A1C2 the carboxylate is substituted by a primary amide (via the Glu362Gln mutation), the same hydrogen bond cannot be made, and thus the second oxygen of the inhibitor is free to make interactions elsewhere.

Another common feature of MMP inhibitors is the placement of a hydrogen bond acceptor at the active site "hot spot" described above. In this case, the hot spot is occupied by one of the oxygen atoms of the sulfonamide group of Compound 1. The O—N distances to the backbone NHs of Leu330 and Gly331 are 2.7 Å and 3.1 Å, respectively.

Typically the side chains of each amino acid of a polypeptide substrate are involved in the specificity of a substrate/protease interaction. The side chain of each substrate residue is recognized by regions of the enzyme which are collectively called sub-sites. The generally accepted nomenclature for the protease sub-sites and their corresponding substrate residues follows, where the double slash represents the position of bond cleavage. Protease sub-sites: S4, S3, S2, S1, S1', S2', S3', S4'; substrate residues: P4, P3, P2, P1, // P1', P2', P3', P4'. Another common feature of known MMP inhibitors is the presence of a P1' group, an inhibitor group that fills the S1' pocket of the active site. This is likely due to the fact that the S1' pocket is typically a very large, hydrophobic pocket, and thus inhibitors that utilize this space can gain free energy by the hydrophobic effect. In this Agg-1 structure, the S1' pocket is in fact a channel that spans approximately 15 Å, and is completely filled by the inhibitor.

Several interactions between Compound 1 and Agg-1-A1C2 are less common among known MMP inhibitors. For example, there is a favorable π stacking interaction between the biphenyl π system and His361 of the active site (~3.7 Å separation). There is also a second π stacking interaction between the P1' phenyl ring and Phe357 (~3.7 Å separation). Finally, there is a water mediated (2.5 Å) hydrogen bond between the carbonyl oxygen of the P1' group and the backbone atoms of αB. The inhibitor-protein interactions are illustrated in FIG. 12.

The overall structure of the Agg-1-A1C2 (see FIG. 2) polypeptide is similar to the Agg-1-A1C2 polypeptide bound to Compound 1. When superimposed, the two structures show an r.m.s. deviation of 1.4 Å for the 280 equivalent Cα-pairs. However, the architecture of the active site in the unbound form shows significant conformational changes compared to the inhibitor-bound form. These changes include reconfiguration of the S-loop and positional rearrangement of residues therein. Electron density maps (FIG. 10) revealed that in the unliganded structure the entire region from Leu321 up to Leu330 is looped toward the active site, completely blocking the entrance to the S' pocket. Although local, the rearrangement is quite significant with displacements of ~2.7 Å and ~6.6 Å for the Cα-atoms of Cys322 and Cys327, respectively. In this position, the Cys322-Cys327 disulfide bridge is maintained, and this bridge stabilizes the displacement of the loop and the "inhibitory" conformation. An unanticipated feature of this arrangement is that residues following Cys327, Asp328 and Thr329, insert their side chains into a pocket near the catalytic $Zn^{2+}$ ion, where the carboxylate group of Asp328 chelates to the metal atom (see FIG. 11). Hence, the S-loop appears to be an "autoinhibitory" element in two aspects. First, it precludes enzyme-substrate recognition by physically occupying the space where peptide substrates would bind, and second, Asp328 prevents the Zn atom from becoming enzymatically active until Asp328 is removed. These data suggest that the binding pocket opens upon interaction with ligands.

Example 2

Aggrecanase-2/Batimastat Complex was Crystallized and its Structure Determined

A recombinant human Agg-2 polypeptide was expressed from CHO cells. The expressed Agg-2 polypeptide included the enzyme's catalytic domain, disintegrin-like domain, and thrombospondin-like domain, and a Strep-tag® (IBA, St. Louis, Mo.) fused to amino acid Phe628 of the protein, truncating the polypeptide at the C-terminus (FIG. 3). A three amino acid linker was included immediately following the spatially conserved phenylalanine preceding the Strep-tag®. CHO cell lines expressing Agg-2 were established by transfecting the Agg-2_Phe628_Strep construct into CHO/DUKX cells using the manufacturers recommended protocol for lipofection (In Vitrogen, Carlsbad, Calif.). Clones were selected in 0.02, 0.05 and 0.1 µM methotrexate. Cell lines expressing the highest level of the recombinant protein were selected by monitoring the recombinant protein in CHO conditioned media by Western blotting using an anti-streptavidin antibody conjugated to horseradish peroxidase (HRP) (Southern Biotech, Birmingham, Ala.) followed by ECL chemiluminescence (Amersham Biosciences, Piscataway, N.J.) and autoradiography.

Concentrated condition media expressing Agg-2_Phe628_Strep were diluted three fold with buffer A (20 mM Tris-Cl, pH 8.0, 5 mM $CaCl_2$, 10 µM $ZnCl_2$, 50 mM NaCl) and loaded onto a Poros® HS (Applied Biosystems, Foster City, Calif.) anion exchange column pre-equilibrated with buffer A. The column was washed and developed by a NaCl gradient up to 1.0 M in the same buffer. Agg-2-containing fractions were pooled and subjected to Strep-Tactin (IBA GmbH, Göttingen, Germany) affinity chromatography in buffer B (20 mM Tris.Cl, pH 8.0, 5 mM $CaCl_2$, 10 µM $ZnCl_2$, 150 mM NaCl). The column was washed and Agg-2 protein was eluted with 2.5 mM Desthiobiotin in buffer B. A Superdex-200 gel filtration column was used to further purify the protein using buffer C (20 mM Tris pH 8.5, 5 mM $CaCl_2$, 10 µM $ZnCl_2$, 50 mM NaCl) as the mobile phase. The resulting Agg-2 containing fractions were pooled and concentrated to 5 mg/mL for crystallography studies.

Inhibitor-bound Agg-2 was obtained by incubating the concentrated protein with 1.2 molar excess of the inhibitor, batimastat. Crystals were grown by hanging drop technique at 18° C. using 10% PEG 8K; 0.2 M NaCl; 0.1 M CHES pH 9.5 as a precipitating solution. Crystals belonged to the space group $P3_1$ and had unit cell parameters a=93.64 Å, b=93.64 Å, c=92.59 Å, and γ=120°, with 2 molecules per crystallographic asymmetric unit. For data collection, the crystal was transferred to the solution containing the crystallization reagent (10% PEG 8K, 0.2 M NaCl; 0.1 M CHES, pH 9.5) plus 25% glycerol, and then flash-frozen in the liquid nitrogen at 100K.

The structure of the Agg-2/Batimastat complex was determined by molecular replacement method using AMORE (Navaza, *Acta Crystallogr.* A50:157-163, 1994) and the structure of Agg-1-A1C2 bound to Compound 1 as a search model. Diffraction data were collected to 2.9 Å resolution at the Advanced Light Source (Berkeley, Calif.), processed and reduced with MOSFLM and SCALA ("The CCP4 Suite: Programs for Protein Crystallography," *Acta Crystallogr.* Sect. D 50:760-763, 1994). Analysis of probability distribution for intensities showed that the crystal is merohedrally twinned, with a twinning fraction of 0.42. Rebuilding in QUANTA and refinement in CNS (Brunger et al., *Acta Crystallogr.* Sect. D 54:905-921, 1997) were performed taking twinning into account. Statistics for data collection and refinement are shown in Table 3.

TABLE 3

Statistics of X-Ray Diffraction Data Collection Agg-2/Batimastat complex

| | |
|---|---|
| Crystal System | Trigonal/monohedral |
| Space Group | $P3_1$ |
| Unit Cell Dimensions | a = 93.64 Å, b = 93.64 Å, c = 92.59 Å, γ = 120° |
| Data Collection Temperature | |
| Number of crystals | 1 |
| Radiation Source | Quantum 4 CCD area detector at ALS (Berkeley, CA) |
| X-ray wavelength | 1.0 Å |
| Resolution range of data | 30.0-2.9 Å |
| Maximum Resolution | 2.9 Å |
| $R_{merge}^a$ | 15% (73%) |
| Completeness | 97.2% |
| Redundancy | 2.5 |
| Total reflections | |
| Unique reflections | 19,567 |
| I/σ(I) | 4.2 (1.0) |
| Phasing and Refinement | |
| Model for molecular refinement | Agg-1/Compound 1 |
| Construct (amino acids) | Agg-2_Phe628_Strep |
| Compounds (ligands) | Batimastat |
| Agg-2_Phe628_Strep molecules per asymmetric unit | 2 |
| Resolution range of refinement | 30.0-2.9 Å |
| $R_{work}^b$ | 23.8% |
| $R_{free}^c$ | 27.3% |
| Number of non-hydrogen protein atoms | |
| Number of water molecules | 62 |
| RMS deviations from ideal bond lengths | 0.009 |
| RMS deviations from ideal bond angles | 1.6 |

$^a R_{merge} = |I_h - <I_h>|/I_h$, where $<I_h>$ is the average intensity over symmetry equivalents.
$^b R_{work} = ||F_{obs}| - |F_{calc}||/|F_{obs}|$
$^c R_{free}$ = is equivalent to $R_{work}$, but calculated for a randomly chosen 5% of reflections omitted from the refinement process.

The structural coordinates of the refined model of the Agg-2/batimastat polypeptide are presented below in Table 6. The columns and designations of Table 6 are as described for Table 5, except the residue designation "WAY" identifies batimastat atoms.

A ribbon diagram of the structure of the Agg-2/Batimastat structure is shown in FIG. 8. The N-terminal residues 265-476 form the catalytic domain of the enzyme and the C-terminal residues 486-556 form the disintegrin-like domain. No electron density was observed for the thrombospondin-like domain, residues 557-628, suggesting that this region is disordered in the crystal structure. The catalytic domain and disintegrin-like domain are connected by a 9-residue cross-over linker (residues 477-486) that extends across the surface of the catalytic domain on the side opposite to the zinc-binding region.

The catalytic domain of Agg-2 reveals a characteristic polypeptide fold that shares structural features with the zinc-peptidase superfamily. It has an α/β structure consisting of six α-helices (αA-αF) surrounding a core of five β-strands (βA-βE) and topologically is more similar to snake venom metalloproteinases (SVMP) than to MMPs. The catalytic zinc environment involves the characteristic zinc-chelating motif $^{410}$HexxHxxGxxH$^{420}$ (SEQ ID NO: 5) with three histidines (His410, His414 and His420) coordinating the zinc atom and the Met-turn motif $^{438}$xMx$^{440}$ with the invariant methionine (Met439) essential for the structural integrity of the zinc-binding site.

In contrast to SVMPs that range from one- to three-disulfide proteinases, the structural arrangement of Agg-2 in the Agg-2/Batimastat complex is supported by four disulfide bridges formed between cysteines that are conserved in the ADAMTS family: Cys342-Cys394, Cys371-Cys376, Cys388-Cys471 and Cys426-Cys455. Among these, the Cys388-Cys471 disulfide connection has a structural equivalent in all of the SVMP structures, but the others seem to be unique to aggrecanases. The Cys342-Cys394 bridge anchors the long αC helix (Cys342) to the β-sheet (Cys394), the Cys371-Cys376 disulfide tethers sequentially distant parts of the S-shaped loop ("S-loop") and the Cys426-Cys455 connection anchors the small αE helix (Cys426) against the C-terminal helix αF (Cys455). In addition, there are three calcium ions, identified from the large peaks in the electron density. One Ca$^{2+}$ ion is found near the Cys371-Cys376 disulfide bridge, forming contacts to three carbonyl oxygens (Leu370, Cys371, Thr378) and three carboxylate oxygens (Asp369, Glu398). Another site, harboring two calcium ions, is in the vicinity of the Cys388-Cys471 bridge, in a location similar to the calcium-binding site in SVMPs. However, in Agg-2 this region is highly charged, allowing for two calcium ions instead of the one seen in the SVMPs structures of atrolysin C or adamalysin II. The two Ca$^{2+}$ ions are separated by 4.8 Å and coordinate with three aspartates (Asp353, Asp360, Asp474), one glutamate (Glu270) and two carbonyl groups (Asp353, Cys471). Comparative amino acid sequence analysis aligned with the Agg-2 structure indicates that residues coordinating the calcium ions at both sites have a high level of conservation across the aggrecanase family.

The disintegrin-like domain of Agg-2 reveals a unique structure made up of two small α-helices followed by two highly twisted antiparallel β-sheets. Each β-sheet has three short β-strands interrupted by irregular connections and long loops. This arrangement is held in place by four disulfide bridges between eight conserved cysteines: Cys497-Cys519, Cys508-Cys529, Cys514-Cys548, and Cys542-Cys553. The orientation of this domain is maintained by a number of electrostatic and hydrophobic interactions with the catalytic domain.

The active site of Agg-2 is very similar to that of the MMPs and SVMPs (Rush and Powers, *Current Topics in Med. Chem.* 4:1311-1327, 2004; Skiles et al., *Current Med. Chem.* 8:425-474, 2001). In general, the active site is broadly defined by a narrow concave groove on the surface of the catalytic domain that runs parallel to βD. At the center of this groove is the catalytic Zn, which is key to protease activity as it activates the water molecule responsible for the hydrolysis of the substrate's peptide bond. As indicated above, the Nitrogen atoms of Histidines 410, 414 and 420 coordinate the catalytic Zn of Agg-2. Also common to other protease active sites are the presence of several inward-facing pockets and solvent-facing grooves adjacent to the major active site groove. These features allow the protein to accommodate side chains of the substrate and are therefore useful for distinguishing side chains for selectivity. Finally, a hydrogen bond acceptor "hot spot" near the catalytic Zn may stabilize the substrate via a hydrogen bond to one of the protein's amide carbonyls. In Agg-2, this "hot spot" is located at a tight turn in the backbone preceding βD and is formed by the two inward facing backbone NHs of Leu379 and Gly380.

The strongest enthalpic interactions between the batimastat and Agg-2 are likely to be the interaction of the hydroxamic moiety with various components of the active site. In this and previously reported batimastat/MMP structures, the hydroxamate interacts with both the active site Zn (O—Zn distances of 2.1 Å and 2.6 Å) and the carboxylate sidechain of the catalytic glutamic acid (Glu411 in Agg-2) via Hydrogen bonding (O—O distance of 2.4 Å). These interactions are likely to contribute significantly to the enthalpy of the protein-ligand interaction.

Batimastat is essentially a peptidomimetic inhibitor, and as such, interacts with the protein in an extended, beta-sheet-like conformation. Its three "sidechains" (the thiophene, isobutyl and benzyl substituents) interact with successive substrate binding pockets, while the two backbone amide groups make four beta-sheet-like H-bonds with the protein. In Agg-2, the thiophene, isobutyl and benzyl sidechains occupy the S1, S1' and S2' sites respectively, while the intervening amide groups hydrogen bond to the backbone atoms of Asp377, Leu379, Ser441, and Leu443 (S1, S1' and S2' represent sub-sites in the Agg-2 binding site) (FIG. 13). The heavy atom distances of these Hydrogen bonds are observed to be 2.8 Å, 3.1 Å, 2.7 Å and 2.7 Å, respectively.

Lengthy table referenced here

US07625731-20091201-T00001

Please refer to the end of the specification for access instructions.

Lengthy table referenced here

US07625731-20091201-T00002

Please refer to the end of the specification for access instructions.

Lengthy table referenced here

US07625731-20091201-T00003

Please refer to the end of the specification for access instructions.

Other embodiments are in the claims.

LENGTHY TABLES

The patent contains a lengthy table section. A copy of the table is available in electronic form from the USPTO web site (http://seqdata.uspto.gov/?pageRequest=docDetail&DocID=US07625731B2). An electronic copy of the table will also be available from the USPTO upon request and payment of the fee set forth in 37 CFR 1.19(b)(3).

What is claimed is:

1. A crystallized polypeptide-ligand complex, comprising:
a human aggrecanase-2 polypeptide comprising amino acid residues 262 to 628 of SEQ ID NO:3, and
a ligand having the structure:

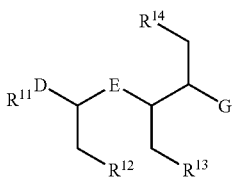

wherein D and E represent an amide or a mimic thereof; wherein $R^{11}$ is methyl, ethyl or propyl, and wherein $R^{12}$, $R^{13}$, and $R^{14}$ is selected from the group consisting of a $C_1$-$C_6$ alkyl, $C_2$-$C_6$ alkenyl, $C_2$-$C_6$ alkynyl, cycyl, heterocyclyl, aryl, heteroaryl cycyloxy, heterocycloxy, aryloxy, heteroaryloxy, cyclylthio, heterocyclylthio, arylthio, heteroarylthio, cyclylalkyl, heterocyclylalkyl, arylalkyl, and heteroarylalkyl; and G is a metal chelating moiety selected from the group consisting of a carboxylic acid, carboxylic amide and hydroxamic acid; and
wherein the crystallized polypeptide-ligand complex has space group $P3_1$ and unit cell dimensions a=93.64 Å, b=93.64 Å, c=92.59 Å, and γ=120°.

2. The crystallized polypeptide-ligand complex of claim 1, wherein the ligand is an inhibitor of aggrecanase activity, wherein said aggrecanase activity is cleavage of cartilage aggrecan.

3. The crystallized polypeptide-ligand complex of claim 1, wherein $R^{12}$ is a phenyl moiety.

4. The crystallized polypeptide-ligand complex of claim 3, wherein $R^{13}$ is an isopropyl moiety.

5. The crystallized polypeptide-ligand complex of claim 4, wherein $R^{14}$ is a heteroarylthio moiety.

6. The crystallized polypeptide-ligand complex of claim 1, wherein the ligand is a peptidomimetic compound.

7. The crystallized polypeptide-ligand complex of claim 1, wherein the ligand is a matrix metalloproteinase inhibitor.

8. The crystallized polypeptide-ligand complex of claim 1, wherein the ligand is batimastat.

9. The crystallized polypeptide-ligand complex of claim 1, wherein the aggrecanase-2 polypeptide consists of amino acid residues 262 to 628 of SEQ ID NO:3.

10. The crystallized polypeptide-ligand complex of claim 1, wherein the aggrecanase-2 polypeptide consists of amino acid residues 262 to 628 of SEQ ID NO:3, and a linker fused to the C-terminal end of said aggrecanase-2 polypeptide.

11. The crystallized polypeptide-ligand complex of claim 1, wherein the ligand is bound to the catalytic domain of the aggecanase-2 polypeptide.

12. The crystallized polypeptide-ligand complex of claim 1, wherein the crystallized complex comprises two molecules of the complex in an asymmetric unit.

13. The crystallized polypeptide-ligand complex of claim 1, wherein the ligand interacts with the aggrecanase-2 polypeptide in an extended beta-sheet-like conformation.

14. The crystallized polypeptide-ligand complex of claim 1, wherein the complex is capable of diffracting X-rays to a resolution of at least 3.0 Å.

15. The crystallized polypeptide-ligand complex of claim 1, wherein the complex is capable of diffracting X-rays to a resolution of at least 2.9 Å.

16. The crystallized polypeptide-ligand complex of claim 1, wherein the complex is capable of diffracting X-rays to a resolution of at least 3.5 Å.

17. The crystallized polypeptide-ligand complex of claim 1, wherein the three-dimensional structure of the complex comprises the structural coordinates of Table 6, ±a root mean square deviation for alpha carbon atoms of not more than 1.5 Å.

18. The crystallized polypeptide-ligand complex of claim 1, wherein the ligand binds a zinc atom located in the active site of the aggrecanase-2 polypeptide.

19. The crystallized polypeptide-ligand complex of claim 1, wherein the ligand binds one or more of Glu411, Asp377, Leu379, Ser441, and Leu443 of the aggrecanase-2 polypeptide as set forth in SEQ ID NO:3.

20. A crystallized polypeptide-ligand complex, comprising:
a human aggrecanase-2 polypeptide, wherein the aggrecanase-2 polypeptide comprises the amino acid residues 262 to 628 of SEQ ID NO:3; and
batimastat,
wherein the crystallized polypeptide-ligand complex has space group $P3_1$ and unit cell dimensions a=93.64 Å, b=93.64 Å, c=92.59 Å, and γ=120°; and diffracts X-rays to a resolution of at least 3.0 Å.

21. A composition comprising the crystallized polypeptide-ligand complex of claim 20 and a carrier.

22. The crystallized polypeptide-ligand complex of claim 20, wherein the wherein the crystallized complex comprises two molecules of the complex in an asymmetric unit.

23. The crystallized polypeptide-ligand complex of claim 22, wherein the ligand binds one or more of Glu411, Asp377, Leu379, Ser441, and Leu443 of the aggrecanase-2 polypeptide as set forth in SEQ ID NO:3.

24. The crystallized polypeptide-ligand complex of claim 23, wherein the three-dimensional structure of the complex comprises the structural coordinates of Table 6, ±a root mean square deviation for alpha carbon atoms of not more than 1.5 Å.

25. The crystallized polypeptide-ligand complex of claim 1, wherein D is an amide, E is an amide, $R^{11}$ is methyl, $R^{12}$ is phenyl, $R^{13}$ is isopropyl, $R^{14}$ is heteroarylthio, and G is hydroxamic acid.

* * * * *